US012788580B2

(12) United States Patent
Emstad et al.

(10) Patent No.: US 12,788,580 B2
(45) Date of Patent: Nov. 10, 2026

(54) EXPANDABLE INTERVERTEBRAL IMPLANT

(71) Applicant: Elevation Spine, Inc., Salinas, CA (US)

(72) Inventors: Erik Emstad, Laurel Springs, NC (US); Austin Clemens, Denver, CO (US)

(73) Assignee: Elevation Spine, Inc., Monterey, CA (US)

( * ) Notice: Subject to any disclaimer, the term of this patent is extended or adjusted under 35 U.S.C. 154(b) by 0 days.

(21) Appl. No.: 19/060,703

(22) Filed: Feb. 23, 2025

(65) Prior Publication Data

US 2025/0268722 A1 Aug. 28, 2025

Related U.S. Application Data

(60) Provisional application No. 63/557,480, filed on Feb. 24, 2024.

(51) Int. Cl.
*A61F 2/44* (2006.01)
*A61F 2/30* (2006.01)

(52) U.S. Cl.
CPC ............ *A61F 2/447* (2013.01); *A61F 2/4455* (2013.01); *A61F 2002/30518* (2013.01); *A61F 2002/30537* (2013.01)

(58) Field of Classification Search
CPC .......................................... A61F 2/4455–2/447
See application file for complete search history.

(56) References Cited

U.S. PATENT DOCUMENTS

| | | | |
|---|---|---|---|
| 5,171,278 | A | 12/1992 | Pisharodi |
| 5,653,763 | A | 8/1997 | Errico et al. |
| 5,665,122 | A | 9/1997 | Kambin |
| 5,693,100 | A | 12/1997 | Pisharodi |
| 6,129,763 | A | 10/2000 | Chauvin et al. |
| 6,159,244 | A | 12/2000 | Suddaby |
| 6,174,334 | B1 | 1/2001 | Suddaby |
| 6,193,757 | B1 | 2/2001 | Foley et al. |
| 6,436,140 | B1 | 8/2002 | Liu et al. |
| 6,641,614 | B1 | 11/2003 | Wagner et al. |
| 6,723,126 | B1 | 4/2004 | Berry |
| 6,905,512 | B2 | 6/2005 | Paes et al. |

(Continued)

FOREIGN PATENT DOCUMENTS

| | | | |
|---|---|---|---|
| CN | 201861800 | U | 6/2011 |
| EP | 2677969 | B1 | 8/2017 |

(Continued)

*Primary Examiner* — Julianna N Harvey
(74) *Attorney, Agent, or Firm* — Schwegman, Lundberg & Woessner, P.A.

(57) ABSTRACT

An expandable intervertebral implant may include a superior endplate configured to engage a superior vertebra, and an inferior endplate configured to engage an inferior vertebra, wherein the inferior endplate may be spaced apart from the superior endplate by a gap. The expandable intervertebral implant may further include a first slider moveable along a first direction to urge linear expansion of the gap, and one or more cams each coupled to the first slider. The one or more cams may be configured to urge angular expansion of the gap in response to at least one of: rotation of the one or more cams about a rotation axis, and motion of the one or more cams along the first direction.

23 Claims, 15 Drawing Sheets

(56) References Cited

U.S. PATENT DOCUMENTS

| | | | |
|---|---|---|---|
| 7,094,257 | B2 | 8/2006 | Mujwid et al. |
| 7,410,501 | B2 | 8/2008 | Michelson |
| 7,569,074 | B2 | 8/2009 | Eisermann et al. |
| 7,655,043 | B2 | 2/2010 | Peterman et al. |
| 7,655,046 | B2 | 2/2010 | Dryer et al. |
| 7,674,296 | B2 | 3/2010 | Rhoda et al. |
| 7,749,270 | B2 | 7/2010 | Peterman |
| 7,753,958 | B2 | 7/2010 | Gordon et al. |
| 7,951,180 | B2 | 5/2011 | Moskowitz et al. |
| 7,967,867 | B2 | 6/2011 | Barreiro et al. |
| 7,985,256 | B2 | 7/2011 | Grotz et al. |
| 8,062,375 | B2 | 11/2011 | Glerum et al. |
| 8,110,004 | B2 | 2/2012 | Valdevit et al. |
| 8,118,870 | B2 | 2/2012 | Gordon et al. |
| 8,192,495 | B2 | 6/2012 | Simpson et al. |
| 8,221,502 | B2 | 7/2012 | Branch, Jr. et al. |
| 8,303,663 | B2 | 11/2012 | Jimenez et al. |
| 8,353,963 | B2 | 1/2013 | Glerum |
| 8,357,181 | B2 | 1/2013 | Lange et al. |
| 8,366,777 | B2 | 2/2013 | Matthis et al. |
| 8,377,133 | B2 | 2/2013 | Yuan et al. |
| 8,394,143 | B2 | 3/2013 | Grotz et al. |
| 8,398,713 | B2 | 3/2013 | Weiman |
| 8,409,286 | B2 | 4/2013 | McKay |
| 8,480,741 | B2 | 7/2013 | Grotz |
| 8,486,149 | B2 | 7/2013 | Saidha |
| 8,523,944 | B2 | 9/2013 | Jimenez |
| 8,551,173 | B2 | 10/2013 | Lechmann |
| 8,574,300 | B2 | 11/2013 | McManus |
| 8,628,576 | B2 | 1/2014 | Triplett |
| 8,663,329 | B2 | 3/2014 | Ernst |
| 8,679,183 | B2 | 3/2014 | Glerum |
| 8,685,098 | B2 | 4/2014 | Glerum |
| 8,696,751 | B2 | 4/2014 | Ashley |
| 8,702,798 | B2 | 4/2014 | Matthis |
| 8,845,731 | B2 | 9/2014 | Weiman |
| 8,845,734 | B2 | 9/2014 | Weiman |
| 8,852,243 | B2 | 10/2014 | Morgenstern Lopez |
| 8,852,279 | B2 | 10/2014 | Weiman |
| 8,894,710 | B2 | 11/2014 | Simpson |
| 8,894,712 | B2 | 11/2014 | Varela |
| 8,926,704 | B2 | 1/2015 | Glerum |
| 8,936,641 | B2 | 1/2015 | Cain |
| 8,940,052 | B2 | 1/2015 | Lechmann |
| 8,986,387 | B1 | 3/2015 | To |
| 8,992,620 | B2 | 3/2015 | Ashley |
| 9,066,813 | B2 | 6/2015 | Farris |
| 9,119,726 | B2 | 9/2015 | Wei |
| 9,125,757 | B2 | 9/2015 | Weiman |
| 9,198,772 | B2 | 12/2015 | Weiman |
| 9,204,972 | B2 | 12/2015 | Weiman |
| 9,271,777 | B2 | 3/2016 | Nichols |
| 9,351,848 | B2 | 5/2016 | Glerum |
| 9,358,125 | B2 | 6/2016 | Jimenez |
| 9,433,510 | B2 | 9/2016 | Lechmann |
| 9,474,626 | B2 | 10/2016 | Jimenez |
| 9,486,328 | B2 | 11/2016 | Jimenez |
| 9,492,288 | B2 | 11/2016 | Wagner |
| 9,510,955 | B2 | 12/2016 | Marino |
| 9,532,883 | B2 | 1/2017 | McLuen |
| 9,539,106 | B2 | 1/2017 | Boehm |
| 9,539,108 | B2 | 1/2017 | Glerum |
| 9,549,824 | B2 | 1/2017 | McAfee |
| 9,554,918 | B2 | 1/2017 | Weiman |
| 9,561,117 | B2 | 2/2017 | Lechmann |
| 9,572,678 | B2 | 2/2017 | Nichols |
| 9,585,766 | B2 | 3/2017 | Robinson |
| 9,603,717 | B2 | 3/2017 | Ibarra |
| 9,662,223 | B2 | 5/2017 | Matthis |
| 9,713,536 | B2 | 7/2017 | Foley |
| 9,724,204 | B2 | 8/2017 | Hansell |
| 9,750,618 | B1 | 9/2017 | Daffinson |
| 9,770,343 | B2 | 9/2017 | Weiman |
| 9,782,265 | B2 | 10/2017 | Weiman |
| 9,820,865 | B2 | 11/2017 | Sharabani |
| 9,839,527 | B2 | 12/2017 | Robinson |
| 9,855,151 | B2 | 1/2018 | Weiman |
| 9,889,019 | B2 | 2/2018 | Rogers |
| 9,907,673 | B2 | 3/2018 | Weiman |
| 9,913,727 | B2 | 3/2018 | Thommen |
| 9,974,662 | B2 | 5/2018 | Hessler |
| 9,974,664 | B2 | 5/2018 | Emerick et al. |
| 9,980,823 | B2 | 5/2018 | Matthis |
| 9,987,143 | B2 | 6/2018 | Robinson |
| 9,987,146 | B1 | 6/2018 | Lentner |
| 10,004,607 | B2 | 6/2018 | Weiman |
| 10,022,239 | B1 | 7/2018 | Lentner |
| 10,034,767 | B2 | 7/2018 | Baynham |
| 10,052,215 | B2 | 8/2018 | Hessler |
| 10,085,849 | B2 | 10/2018 | Weiman |
| 10,098,757 | B2 | 10/2018 | Logan |
| 10,098,758 | B2 | 10/2018 | Matthews |
| 10,117,755 | B2 | 11/2018 | Emerick |
| 10,137,001 | B2 | 11/2018 | Weiman |
| 10,159,583 | B2 | 12/2018 | Dietzel |
| 10,182,922 | B2 | 1/2019 | Nichols |
| 10,219,914 | B2 | 3/2019 | Faulhaber |
| 10,285,824 | B2 | 5/2019 | Robinson |
| 10,299,935 | B2 | 5/2019 | Loebl |
| 10,322,009 | B2 | 6/2019 | Aghayev |
| 10,350,081 | B2 | 7/2019 | Seifert |
| 10,363,142 | B2 | 7/2019 | McClintock |
| 10,383,741 | B2 | 8/2019 | Butler |
| 10,390,962 | B2 | 8/2019 | Weiman |
| 10,398,563 | B2 | 9/2019 | Engstrom |
| 10,420,654 | B2 | 9/2019 | Logan |
| 10,426,634 | B1 | 10/2019 | Al-Jazaeri |
| 10,492,923 | B2 | 12/2019 | Zur |
| 10,500,059 | B2 | 12/2019 | Grotz |
| 10,507,116 | B2 | 12/2019 | Shoshtaev |
| 10,512,550 | B2 | 12/2019 | Bechtel et al. |
| 10,524,927 | B2 | 1/2020 | Ryan |
| 10,561,502 | B2 | 2/2020 | Bernard et al. |
| 10,653,531 | B2 | 5/2020 | Werner |
| 10,682,239 | B2 | 6/2020 | Hsu |
| 10,682,241 | B2 | 6/2020 | Glerum |
| 10,702,392 | B2 | 7/2020 | Greenhalgh |
| 10,709,571 | B2 | 7/2020 | Iott |
| 10,709,573 | B2 | 7/2020 | Weiman |
| 10,722,377 | B2 | 7/2020 | Glerum |
| 10,722,379 | B2 | 7/2020 | McLaughlin |
| 10,758,367 | B2 | 9/2020 | Weiman |
| 10,779,957 | B2 | 9/2020 | Weiman |
| 10,806,596 | B2 | 10/2020 | Iott |
| 10,835,387 | B2 | 11/2020 | Weiman |
| 10,842,644 | B2 | 11/2020 | Weiman |
| 10,856,997 | B2 | 12/2020 | Cowan |
| 10,869,768 | B2 | 12/2020 | Weiman |
| 10,869,769 | B2 | 12/2020 | Eisen |
| 10,881,524 | B2 | 1/2021 | Eisen |
| 10,881,531 | B2 | 1/2021 | Berry |
| 10,898,344 | B2 | 1/2021 | Alheidt |
| 10,925,752 | B2 | 2/2021 | Weiman |
| 10,945,857 | B2 | 3/2021 | Emstad |
| 10,945,858 | B2 | 3/2021 | Bechtel |
| 10,973,649 | B2 | 4/2021 | Weiman |
| 10,980,642 | B2 | 4/2021 | Glerum |
| 10,980,644 | B2 | 4/2021 | Purcell |
| 11,020,238 | B2 | 6/2021 | Nichols |
| 11,026,800 | B2 | 6/2021 | Seifert |
| 11,033,401 | B2 | 6/2021 | Shoshtaev |
| 11,033,403 | B2 | 6/2021 | Predick |
| 11,090,167 | B2 | 8/2021 | Emerick |
| 11,103,366 | B2 | 8/2021 | Glerum |
| 11,166,826 | B2 | 11/2021 | Huang |
| 11,185,421 | B1 | 11/2021 | Miller |
| 11,191,650 | B2 | 12/2021 | Weiman |
| 11,207,192 | B2 | 12/2021 | Suddaby |
| 11,253,372 | B2 | 2/2022 | Grotz |
| 11,285,014 | B1 | 3/2022 | Josse |
| 11,285,018 | B2 | 3/2022 | Shoshtaev |
| 11,291,554 | B1 | 4/2022 | Prevost |
| 11,304,817 | B2 | 4/2022 | Altarac |
| 11,304,821 | B2 | 4/2022 | Berry |

(56) References Cited

U.S. PATENT DOCUMENTS

| | | | |
|---|---|---|---|
| 11,337,825 B2 | 5/2022 | Predick | |
| 11,344,424 B2 | 5/2022 | Luu | |
| 11,344,430 B2 | 5/2022 | Glerum | |
| 11,376,134 B1 | 7/2022 | Dewey | |
| 11,382,764 B2 | 7/2022 | Predick | |
| 11,395,743 B1 | 7/2022 | Hynes | |
| 11,446,156 B2 | 9/2022 | Hunziker | |
| 11,446,161 B2 | 9/2022 | Rogers | |
| 11,446,162 B2 | 9/2022 | Weiman | |
| 11,452,614 B2 | 9/2022 | Rogers | |
| 11,471,301 B2 | 10/2022 | Jimenez | |
| 11,491,025 B2 | 11/2022 | Gilbride | |
| 11,517,443 B2 | 12/2022 | Dewey | |
| 11,564,724 B2 | 1/2023 | Josse | |
| 11,564,807 B2 | 1/2023 | Iott | |
| 11,602,440 B2 * | 3/2023 | Zakelj | A61F 2/4611 |
| 11,612,499 B2 | 3/2023 | Barfield | |
| 11,660,205 B2 | 5/2023 | Rogers | |
| 11,717,419 B2 | 8/2023 | Altarac | |
| 11,730,608 B2 | 8/2023 | Protopsaltis | |
| 11,759,334 B2 | 9/2023 | Klausman | |
| 12,208,017 B2 | 1/2025 | McLaughlin | |
| 2002/0151977 A1 | 10/2002 | Paes | |
| 2002/0161444 A1 | 10/2002 | Choi | |
| 2003/0135279 A1 | 7/2003 | Michelson | |
| 2004/0088054 A1 | 5/2004 | Berry | |
| 2004/0153156 A1 | 8/2004 | Cohen | |
| 2004/0162618 A1 | 8/2004 | Mujwid | |
| 2005/0010295 A1 | 1/2005 | Michelson | |
| 2005/0131536 A1 | 6/2005 | Eisermann | |
| 2005/0209698 A1 | 9/2005 | Gordon | |
| 2005/0256576 A1 | 11/2005 | Moskowitz | |
| 2005/0273174 A1 | 12/2005 | Gordon | |
| 2006/0009770 A1 | 1/2006 | Speirs | |
| 2006/0129244 A1 | 6/2006 | Ensign | |
| 2006/0149385 A1 | 7/2006 | McKay | |
| 2006/0206207 A1 | 9/2006 | Dryer | |
| 2006/0241770 A1 | 10/2006 | Rhoda | |
| 2007/0093901 A1 | 4/2007 | Grotz | |
| 2007/0100340 A1 | 5/2007 | Lange | |
| 2008/0147194 A1 | 6/2008 | Grotz | |
| 2008/0300598 A1 | 12/2008 | Barreiro | |
| 2009/0210062 A1 | 8/2009 | Thalgott | |
| 2009/0222100 A1 | 9/2009 | Cipoletti | |
| 2010/0049324 A1 | 2/2010 | Valdevit | |
| 2010/0082109 A1 | 4/2010 | Greenhalgh | |
| 2010/0145456 A1 | 6/2010 | Simpson | |
| 2010/0168429 A1 | 7/2010 | Halland | |
| 2010/0185291 A1 | 7/2010 | Jimenez | |
| 2010/0280619 A1 | 11/2010 | Yuan | |
| 2010/0286783 A1 | 11/2010 | Lechmann | |
| 2011/0015747 A1 | 1/2011 | McManus | |
| 2011/0035011 A1 | 2/2011 | Cain | |
| 2011/0093074 A1 | 4/2011 | Glerum | |
| 2011/0130835 A1 | 6/2011 | Ashley | |
| 2011/0160861 A1 | 6/2011 | Jimenez | |
| 2011/0172716 A1 | 7/2011 | Glerum | |
| 2011/0319997 A1 | 12/2011 | Glerum | |
| 2012/0059473 A1 | 3/2012 | Weiman | |
| 2012/0116518 A1 | 5/2012 | Grotz | |
| 2012/0215313 A1 | 8/2012 | Saidha | |
| 2012/0245695 A1 | 9/2012 | Simpson | |
| 2012/0265309 A1 | 10/2012 | Glerum | |
| 2012/0310350 A1 | 12/2012 | Farris | |
| 2012/0323327 A1 | 12/2012 | McAfee | |
| 2013/0053966 A1 | 2/2013 | Jimenez | |
| 2013/0158668 A1 | 6/2013 | Nichols | |
| 2013/0197642 A1 | 8/2013 | Ernst | |
| 2013/0211525 A1 | 8/2013 | McLuen | |
| 2013/0253650 A1 | 9/2013 | Ashley | |
| 2013/0274883 A1 | 10/2013 | McLuen | |
| 2014/0031938 A1 | 1/2014 | Lechmann | |
| 2014/0039622 A1 | 2/2014 | Glerum | |
| 2014/0058519 A1 | 2/2014 | Glerum | |
| 2014/0094917 A1 | 4/2014 | Salerni | |
| 2014/0100660 A1 | 4/2014 | Morgenstern Lopez | |
| 2014/0114420 A1 | 4/2014 | Robinson | |
| 2014/0148904 A1 | 5/2014 | Robinson | |
| 2014/0236296 A1 | 8/2014 | Wagner | |
| 2014/0236297 A1 | 8/2014 | Iott | |
| 2014/0249628 A1 | 9/2014 | Weiman | |
| 2014/0249631 A1 | 9/2014 | Weiman | |
| 2014/0249632 A1 | 9/2014 | Weiman | |
| 2014/0277474 A1 | 9/2014 | Robinson | |
| 2014/0277492 A1 | 9/2014 | Wei | |
| 2014/0277500 A1 | 9/2014 | Logan | |
| 2014/0288652 A1 | 9/2014 | Boehm | |
| 2014/0296984 A1 | 10/2014 | Etminan | |
| 2014/0316522 A1 | 10/2014 | Weiman | |
| 2015/0012097 A1 | 1/2015 | Ibarra | |
| 2015/0012101 A1 | 1/2015 | Glerum | |
| 2015/0018957 A1 | 1/2015 | Nichols | |
| 2015/0066145 A1 | 3/2015 | Rogers | |
| 2015/0073552 A1 | 3/2015 | To | |
| 2015/0088258 A1 | 3/2015 | Jimenez | |
| 2015/0094813 A1 | 4/2015 | Lechmann | |
| 2015/0094814 A1 | 4/2015 | Emerick | |
| 2015/0148908 A1 | 5/2015 | Marino | |
| 2015/0257892 A1 | 9/2015 | Lechmann | |
| 2015/0272743 A1 | 10/2015 | Jimenez | |
| 2015/0272746 A1 | 10/2015 | Jimenez | |
| 2015/0328012 A1 | 11/2015 | Hansell | |
| 2015/0351925 A1 | 12/2015 | Emerick et al. | |
| 2015/0366675 A1 | 12/2015 | Matthews | |
| 2016/0095718 A1 | 4/2016 | Burkhardt | |
| 2016/0106551 A1 | 4/2016 | Grimberg, Jr. | |
| 2016/0151168 A1 | 6/2016 | Weiman | |
| 2016/0166396 A1 * | 6/2016 | McClintock | A61F 2/446 623/17.16 |
| 2016/0242927 A1 | 8/2016 | Seifert et al. | |
| 2016/0250034 A1 | 9/2016 | Loebl | |
| 2017/0000622 A1 | 1/2017 | Thommen | |
| 2017/0035577 A1 | 2/2017 | Iott | |
| 2017/0042695 A1 | 2/2017 | Foley | |
| 2017/0119542 A1 | 5/2017 | Logan | |
| 2017/0128226 A1 | 5/2017 | Faulhaber | |
| 2017/0156884 A1 | 6/2017 | Rathbun | |
| 2017/0156885 A1 | 6/2017 | Zur | |
| 2017/0172760 A1 | 6/2017 | Loebl | |
| 2017/0209282 A1 | 7/2017 | Aghayev | |
| 2017/0216045 A1 * | 8/2017 | Dewey | A61F 2/447 |
| 2017/0216046 A1 | 8/2017 | Greenhalgh | |
| 2017/0224505 A1 | 8/2017 | Butler | |
| 2017/0319352 A1 * | 11/2017 | Dewey | A61F 2/447 |
| 2017/0333198 A1 * | 11/2017 | Robinson | A61F 2/4455 |
| 2017/0354512 A1 | 12/2017 | Weiman | |
| 2018/0000609 A1 | 1/2018 | Hessler | |
| 2018/0036138 A1 * | 2/2018 | Robinson | A61F 2/4611 |
| 2018/0177603 A1 | 6/2018 | Weiman | |
| 2018/0177604 A1 | 6/2018 | Weiman | |
| 2018/0185163 A1 | 7/2018 | Weiman | |
| 2018/0193164 A1 | 7/2018 | Shoshtaev | |
| 2018/0360616 A1 | 12/2018 | Luu | |
| 2018/0368983 A1 | 12/2018 | Werner | |
| 2019/0021873 A1 | 1/2019 | Dmuschewsky | |
| 2019/0070015 A1 | 3/2019 | Emerick | |
| 2019/0117409 A1 | 4/2019 | Shoshtaev | |
| 2019/0254836 A1 | 8/2019 | Cowan | |
| 2019/0269521 A1 | 9/2019 | Shoshtaev | |
| 2019/0274836 A1 | 9/2019 | Eisen | |
| 2019/0274837 A1 | 9/2019 | Eisen | |
| 2019/0298540 A1 | 10/2019 | Aghayev | |
| 2019/0307577 A1 | 10/2019 | Predick | |
| 2019/0321190 A1 | 10/2019 | Wagner | |
| 2019/0321198 A1 | 10/2019 | Glerum | |
| 2019/0336302 A1 | 11/2019 | Seifert | |
| 2019/0388232 A1 | 12/2019 | Purcell | |
| 2020/0078190 A1 | 3/2020 | Rogers | |
| 2020/0129307 A1 | 4/2020 | Hunziker | |
| 2020/0163775 A1 | 5/2020 | Kim | |
| 2020/0281741 A1 | 9/2020 | Grotz | |
| 2020/0315811 A1 | 10/2020 | Cryder | |
| 2020/0352731 A1 | 11/2020 | Berry | |
| 2020/0352738 A1 | 11/2020 | Berry | |

(56) References Cited

U.S. PATENT DOCUMENTS

| | | | | |
|---|---|---|---|---|
| 2020/0390565 | A1 | 12/2020 | Jimenez | |
| 2021/0000160 | A1 | 1/2021 | Olmos | |
| 2021/0045891 | A1 | 2/2021 | Rogers | |
| 2021/0045892 | A1 | 2/2021 | Rogers | |
| 2021/0121300 | A1 | 4/2021 | Weiman | |
| 2021/0137695 | A1 | 5/2021 | Huang | |
| 2021/0186706 | A1 | 6/2021 | Spitler | |
| 2021/0236298 | A1 | 8/2021 | Weiman | |
| 2021/0251770 | A1 | 8/2021 | Purcell | |
| 2021/0322179 | A1 | 10/2021 | Miller | |
| 2021/0346174 | A1 | 11/2021 | Flint | |
| 2021/0353428 | A1 | 11/2021 | Predick | |
| 2021/0378832 | A1 | 12/2021 | Altarac | |
| 2021/0378833 | A1 | 12/2021 | Gray | |
| 2022/0015923 | A1 | 1/2022 | Shoshtaev | |
| 2022/0071772 | A1* | 3/2022 | Lauf | A61F 2/442 |
| 2022/0079770 | A1* | 3/2022 | Miller | A61F 2/4425 |
| 2022/0104951 | A1 | 4/2022 | Predick | |
| 2022/0125596 | A1 | 4/2022 | Valkoun | |
| 2022/0133379 | A1 | 5/2022 | Nayet | |
| 2022/0133492 | A1 | 5/2022 | Josse | |
| 2022/0133496 | A1 | 5/2022 | Dewey | |
| 2022/0133497 | A1 | 5/2022 | Dewey | |
| 2022/0133498 | A1 | 5/2022 | Josse | |
| 2022/0133499 | A1 | 5/2022 | Josse | |
| 2022/0133503 | A1 | 5/2022 | Nayet | |
| 2022/0160515 | A1 | 5/2022 | Bougere | |
| 2022/0168116 | A1 | 6/2022 | Yadav | |
| 2022/0175547 | A1* | 6/2022 | Fresneau | A61F 2/447 |
| 2022/0183854 | A1 | 6/2022 | Altarac | |
| 2022/0211512 | A1 | 7/2022 | Berry | |
| 2022/0265440 | A1 | 8/2022 | Lauf | |
| 2022/0339002 | A1 | 10/2022 | Freedman | |
| 2022/0387184 | A1 | 12/2022 | Josse | |
| 2022/0387190 | A1 | 12/2022 | Klausman | |
| 2022/0409388 | A1 | 12/2022 | Barfield | |
| 2023/0018019 | A1 | 1/2023 | Protopsaltis | |
| 2023/0023033 | A1 | 1/2023 | Eisen | |
| 2023/0026598 | A1 | 1/2023 | Weiman | |
| 2023/0060949 | A1 | 3/2023 | Ahn | |
| 2023/0072719 | A1 | 3/2023 | Rogers | |
| 2023/0095997 | A1 | 3/2023 | Ahn | |
| 2023/0104776 | A1* | 4/2023 | Jimenez | A61F 2/447<br>623/17.16 |
| 2023/0165687 | A1 | 6/2023 | Barrus | |
| 2023/0172724 | A1 | 6/2023 | Hansen | |
| 2023/0172726 | A1 | 6/2023 | Krawiec | |
| 2023/0233333 | A1 | 7/2023 | Linares | |
| 2023/0277330 | A1 | 9/2023 | Stiefferman | |
| 2024/0307191 | A1 | 9/2024 | Siccardi | |
| 2024/0415670 | A1* | 12/2024 | Baynham | A61F 2/447 |
| 2025/0152376 | A1 | 5/2025 | McLaughlin | |

FOREIGN PATENT DOCUMENTS

| | | | |
|---|---|---|---|
| EP | 2931183 | B1 | 5/2018 |
| EP | 3421013 | A1 | 1/2019 |
| EP | 2777632 | B1 | 4/2020 |
| EP | 2830542 | B1 | 10/2021 |
| EP | 3030198 | B1 | 12/2021 |
| EP | 3485850 | B1 | 9/2023 |
| EP | 3614974 | B1 | 11/2024 |
| EP | 3614975 | B1 | 11/2024 |
| WO | WO2013152257 | A1 | 10/2013 |
| WO | WO2016069796 | A1 | 5/2016 |
| WO | WO2019022976 | A1 | 1/2019 |
| WO | WO2020068445 | A1 | 4/2020 |
| WO | WO2020252040 | A1 | 12/2020 |

* cited by examiner

EXPANDABLE INTERVERTEBRAL IMPLANT

CROSS-REFERENCE TO RELATED APPLICATIONS

The present applications claims the benefit of U.S. Provisional Ser. No. 63/557,480, filed on Feb. 24, 2024 and entitled EXPANDABLE INTERVERTEBRAL IMPLANT, which is incorporated by reference as though set forth herein in its entirety.

TECHNICAL FIELD

The present disclosure relates to systems and methods for use in orthopedic surgery. More specifically, the present disclosure relates to expandable intervertebral implant systems and surgical methods.

BACKGROUND

Intervertebral disc degeneration and associated spinal disorders present significant clinical challenges, often leading to chronic pain and reduced mobility in affected individuals. Current surgical interventions primarily involve spinal fusion techniques or the use of fixed-size intervertebral implants. While these approaches aim to stabilize the spine and alleviate symptoms, they often limit natural spinal motion and may contribute to complications such as adjacent segment disease.

Fixed-size intervertebral implants currently available on the market vary in design and material composition but share common limitations. These implants require precise pre-operative sizing and may necessitate intraoperative adjustments to ensure proper fit within the disc space. Surgeons may also face challenges in adapting these implants to individual patient anatomy and achieving optimal alignment post-implantation. Moreover, the complexity of implantation procedures can prolong surgery times and recovery periods for patients.

Recognizing these challenges, there is a growing demand for intervertebral implants that offer greater versatility and precision in surgical application. An ideal solution would provide adjustable sizing capabilities intraoperatively, facilitating tailored fitment to varying disc spaces and spinal geometries. Such advancements could potentially improve surgical outcomes, minimize recovery times, and reduce the incidence of postoperative complications associated with current implant technologies.

SUMMARY

The various systems and methods of the present disclosure have been developed in response to the present state of the art, and in particular, in response to the problems and needs in the art that have not yet been fully solved by currently available expandable intervertebral implant systems and surgical methods.

In some embodiments, an expandable intervertebral implant may include a superior endplate configured to engage a superior vertebra, and an inferior endplate configured to engage an inferior vertebra, wherein the inferior endplate may be spaced apart from the superior endplate by a gap. The expandable intervertebral implant may further include a first slider moveable along a first direction to urge linear expansion of the gap, and one or more cams each coupled to the first slider. The one or more cams may be configured to urge angular expansion of the gap in response to at least one of: rotation of the one or more cams about a rotation axis, and motion of the one or more cams along the first direction.

In the expandable intervertebral implant of any preceding paragraph, the expandable intervertebral implant may further include a second slider threadably coupled to the first slider. The second slider may be moveable along the first direction, the second slider may be moveable independent of the first slider, and movement of the second slider may result in at least one of: rotation of the one or more cams about the rotation axis, and motion of the one or more cams along the first direction.

In the expandable intervertebral implant of any preceding paragraph, the expandable intervertebral implant may further include a first screw, extending along an anterior-posterior direction, configured to rotatably engage the first slider. The first direction may include the anterior-posterior direction, and rotation of the first screw may result in movement of the first slider in the anterior-posterior direction.

In the expandable intervertebral implant of any preceding paragraph, the first screw may be captive relative to the second slider.

In the expandable intervertebral implant of any preceding paragraph, the expandable intervertebral implant may further include a second screw, extending along the anterior-posterior direction, configured to rotatably engage the second slider. The second screw may be configured to rotate to urge movement of the second slider in the anterior-posterior direction.

In the expandable intervertebral implant of any preceding paragraph, the second screw may be captive relative to the superior endplate.

In the expandable intervertebral implant of any preceding paragraph, the one or more cams may be configured to be rotatable and translatable relative to the superior endplate and the inferior endplate.

In some embodiments, an expandable intervertebral implant may include a superior endplate configured to engage a superior vertebra, and an inferior endplate configured to engage an inferior vertebra, wherein the inferior endplate may be spaced apart from the superior endplate by a gap. The expandable intervertebral implant may further include one or more cams configured to be translatable relative to the superior endplate and the inferior endplate, a first screw extending along an anterior-posterior direction, and a first slider configured to threadably receive the first screw. The first screw may be configured to rotate to urge translation of the first slider in the anterior-posterior direction, the one or more cams may be coupled to the first slider such that translation of the first slider in the anterior-posterior direction results in translation of the one or more cams, and the one or more cams may be configured to urge angular expansion of the gap in response to translation of the one or more cams.

In the expandable intervertebral implant of any preceding paragraph, the expandable intervertebral implant may further include a second slider threadably coupled to the first slider and a second screw extending along the anterior-posterior direction. The second slider may be moveable along the anterior-posterior direction, the second screw may be configured to rotate to urge movement of the second slider in the anterior-posterior direction, and movement of the second slider may urge linear expansion of the gap.

In the expandable intervertebral implant of any preceding paragraph, the first slider may be moveable independent of the second slider.

In the expandable intervertebral implant of any preceding paragraph, movement of the second slider may result in comparable movement of the first slider and movement of the first slider may not result in movement of the second slider.

In the expandable intervertebral implant of any preceding paragraph, the one or more cams may be further configured to be rotatable relative to the superior endplate and the inferior endplate, wherein translation of the first slider in the anterior-posterior direction may result in rotation of the one or more cams, and the one or more cams may be configured to urge angular expansion of the gap in response to rotation of the one or more cams.

In the expandable intervertebral implant of any preceding paragraph, the expandable intervertebral implant may further include an anterior height having a first distance, in a superior-inferior plane, between a superior anterior portion and an inferior anterior portion, and a posterior height having a second distance, in the superior-inferior plane, between a superior posterior portion and an inferior posterior portion. In response to rotation of the one or more cams about a medial-lateral axis, the one or more cams may be configured to urge angular expansion of the gap by increasing the anterior height more than the posterior height.

In the expandable intervertebral implant of any preceding paragraph, the one or more cams may be received within one or more cam slots, and the one or more cam slots may be configured to urge rotation of the one or more cams relative to the first slider in response to translation of the one or more cams within the one or more cam slots.

In some embodiments, an expandable intervertebral implant may include a superior endplate configured to engage a superior vertebra, and an inferior endplate configured to engage an inferior vertebra, wherein the inferior endplate may be spaced apart from the superior endplate by a gap such that the expandable intervertebral implant may include, an anterior height having a first distance, in a superior-inferior plane, between a superior anterior portion of the superior endplate and an inferior anterior portion of the inferior endplate, and a posterior height having a second distance, in the superior-inferior plane, between a superior posterior portion and an inferior posterior portion. The expandable intervertebral implant may further include a first cam configured to rotate about a medial-lateral axis such that the gap may expand linearly and angularly by increasing the posterior height, and increasing the anterior height more than the posterior height.

In the expandable intervertebral implant of any preceding paragraph, the expandable intervertebral implant may further include a first slider coupled to the first cam. The first slider may be moveable along an anterior-posterior direction, and movement of the first slider may result in at least one of: rotation of the first cam about the medial-lateral axis, and motion of the first cam along the anterior-posterior direction.

In the expandable intervertebral implant of any preceding paragraph, the expandable intervertebral implant may further include a first screw, extending along the anterior-posterior direction, configured to rotatably engage the first slider, wherein the first screw may be configured to rotate to urge movement of the first slider in the anterior-posterior direction.

In the expandable intervertebral implant of any preceding paragraph, the first cam may be translatable in an anterior-posterior direction, and, in response to translation of the first cam, the first cam may be configured to urge angular expansion of the gap by increasing the anterior height more than the posterior height.

In the expandable intervertebral implant of any preceding paragraph, the first cam may be received within a cam slot, and the cam slot may be configured to urge rotation of the first cam relative to the cam slot in response to translation of the first cam within the cam slot.

In the expandable intervertebral implant of any preceding paragraph, the expandable intervertebral implant may further include a second slider moveable along a first direction to urge linear expansion of the gap.

These and other features and advantages of the present disclosure will become more fully apparent from the following description and appended claims or may be learned by the practice of the implants, systems, and methods set forth hereinafter.

BRIEF DESCRIPTION OF THE DRAWINGS

Exemplary embodiments of the disclosure will become more fully apparent from the following description and appended claims, taken in conjunction with the accompanying drawings. Understanding that these drawings depict only exemplary embodiments and are, therefore, not to be considered limiting of the scope of the appended claims, the exemplary embodiments of the disclosure will be described with additional specificity and detail through use of the accompanying drawings.

Figure 1:
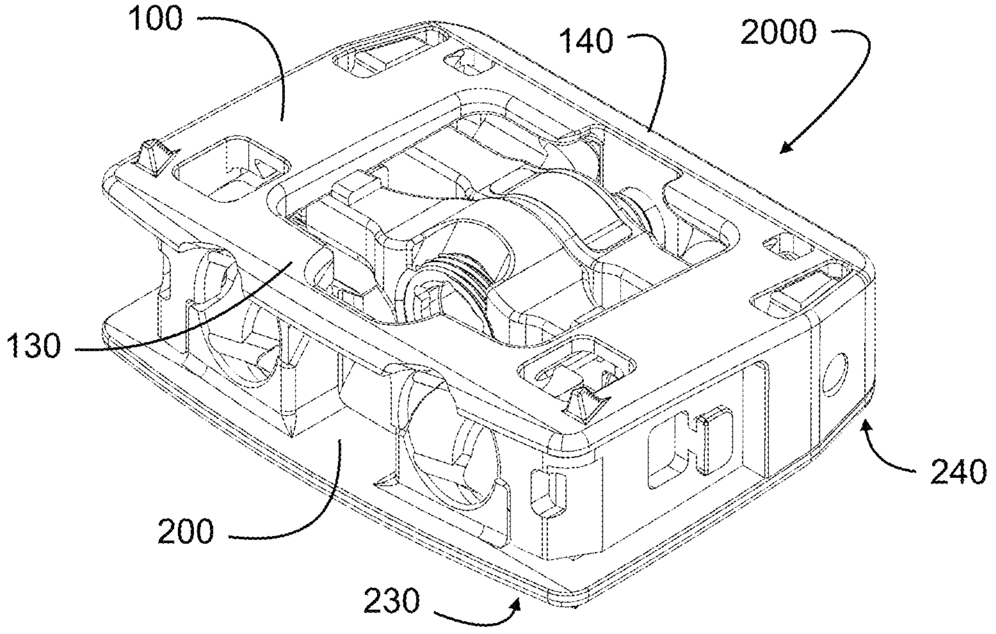
FIG. 1 is a perspective view of an expandable intervertebral implant in a collapsed configuration according to an embodiment of the present disclosure.

It is to be understood that the drawings are for purposes of illustrating the concepts of the present disclosure and may not be drawn to scale. Furthermore, the drawings illustrate exemplary embodiments and do not represent limitations to the scope of the present disclosure.

DETAILED DESCRIPTION

Exemplary embodiments of the present disclosure will be best understood by reference to the drawings, wherein like parts are designated by like numerals throughout. It will be readily understood that the components of the present disclosure, as generally described and illustrated in the drawings, could be arranged, and designed in a wide variety of different configurations. Thus, the following more detailed description of the embodiments of the devices, systems, and methods, as represented in the drawings, is not intended to limit the scope of the present disclosure but is merely representative of exemplary embodiments of the present disclosure.

The word "exemplary" is used herein to mean "serving as an example, instance, or illustration." Any embodiment described herein as "exemplary" is not necessarily to be construed as preferred or advantageous over other embodiments. While the various aspects of the embodiments are presented in the drawings, the drawings are not necessarily drawn to scale unless specifically indicated.

Standard medical planes of reference and descriptive terminology are employed in this specification. While these terms are commonly used to refer to the human body, certain terms are applicable to physical objects in general.

A standard system of three mutually perpendicular reference planes is employed. A sagittal plane divides a body into right and left portions. A coronal plane divides a body into anterior and posterior portions. A transverse plane divides a body into superior and inferior portions. A mid-sagittal, mid-coronal, or mid-transverse plane divides a body into equal portions, which may be bilaterally symmetric. The intersection of the sagittal and coronal planes defines a superior-inferior or cephalad-caudal axis. The intersection of the sagittal and transverse planes defines an anterior-posterior axis. The intersection of the coronal and transverse planes defines a medial-lateral axis. The superior-inferior or cephalad-caudal axis, the anterior-posterior axis, and the medial-lateral axis are mutually perpendicular.

Anterior means toward the front of a body. Posterior means toward the back of a body. Superior or cephalad means toward the head. Inferior or caudal means toward the feet or tail. Medial means toward the midline of a body, particularly toward a plane of bilateral symmetry of the body. Lateral means away from the midline of a body or away from a plane of bilateral symmetry of the body. Axial means toward a central axis of a body. Abaxial means away from a central axis of a body. Ipsilateral means on the same side of the body. Contralateral means on the opposite side of the body. Proximal means toward the trunk of the body. Proximal may also mean toward a user or operator. Distal means away from the trunk. Distal may also mean away from a user or operator. Dorsal means toward the top of the foot. Plantar means toward the sole of the foot. Varus means deviation of the distal part of the leg below the knee inward, resulting in a bowlegged appearance. Valgus means deviation of the distal part of the leg below the knee outward, resulting in a knock-kneed appearance.

The present disclosure relates to intervertebral implant devices, systems, and methods. Those skilled in the art will recognize that the following description is merely illustrative of the principles of the technology, which may be applied in various ways to provide many alternative embodiments. The present disclosure illustrates devices for an anterior lumbar interbody fusion (ALIF) for the purposes of illustrating the concepts of the present design. However, it will be understood that other variations and uses are contemplated including, but not limited to, devices for a posterior lumbar interbody fusion (PLIF), devices for transforaminal lumbar interbody fusion (TLIF), devices for interbody fusion of the thoracic spine, devices for interbody fusion of the cervical spine, etc.

Figure 2:
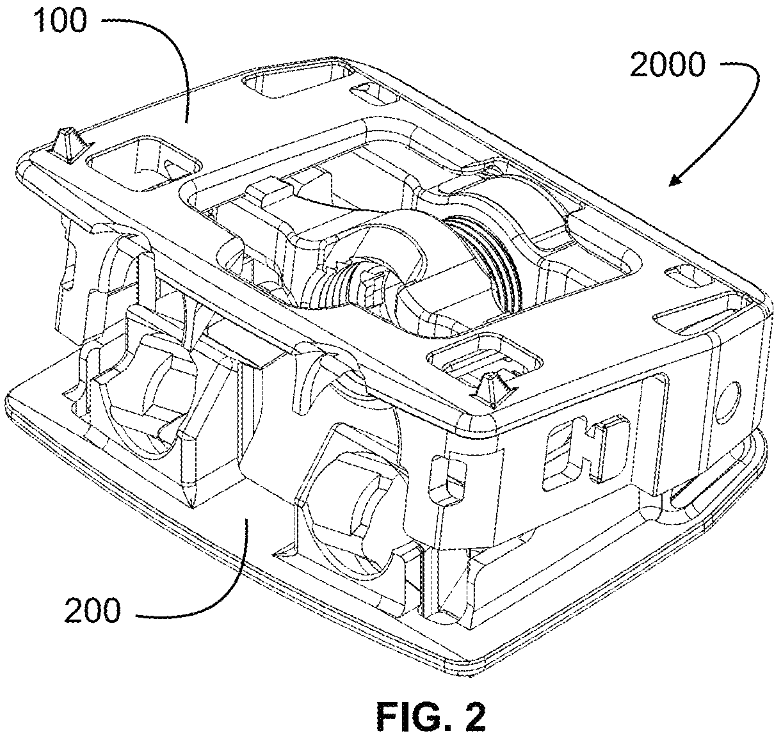
FIG. 2 is a perspective view of the expandable intervertebral implant of FIG. 1 in an expanded configuration.
Figure 3A:
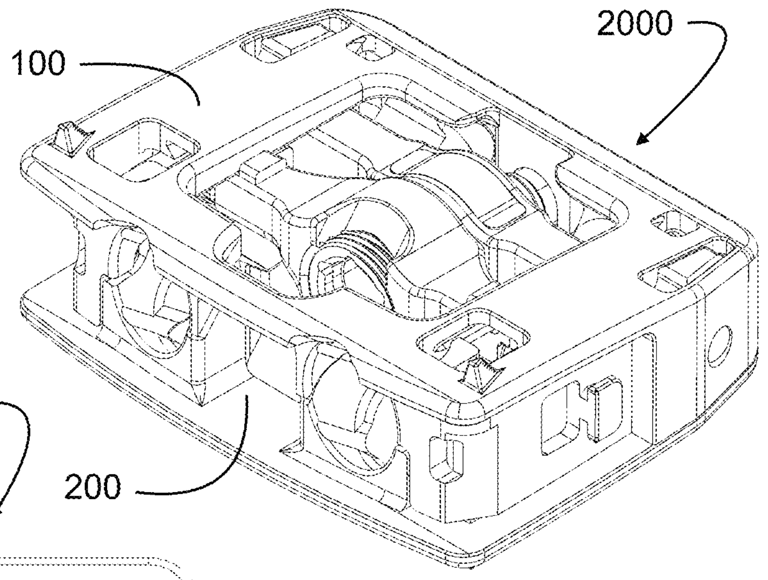
FIGS. 3A, 3B, 3C and 3D are perspective, top, front and side views of the expandable intervertebral implant of FIG. 1 in a collapsed configuration.
Figure 3B:
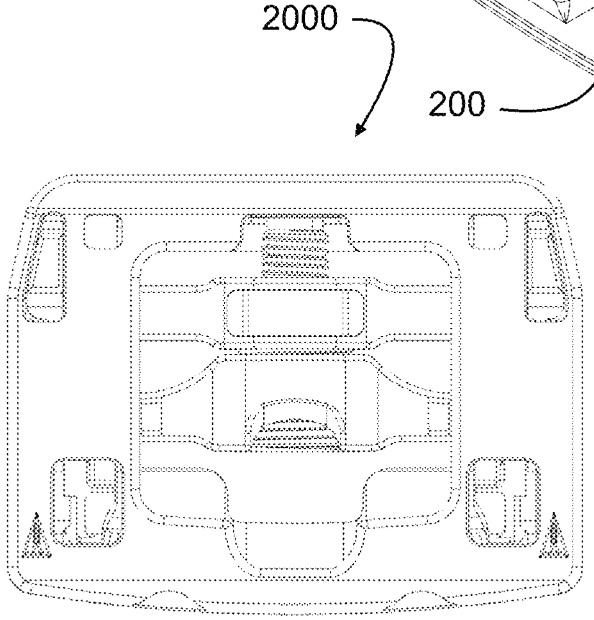
Figure 3C:
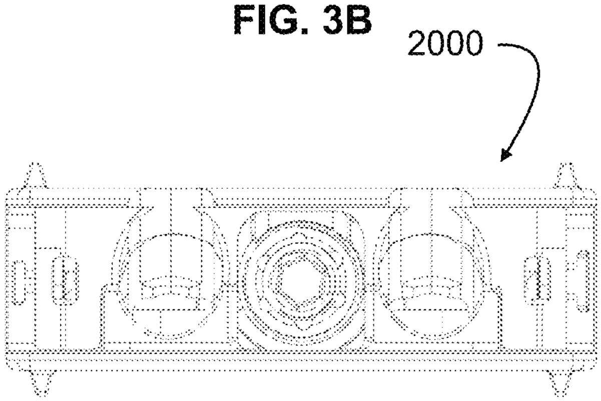
Figure 3D:
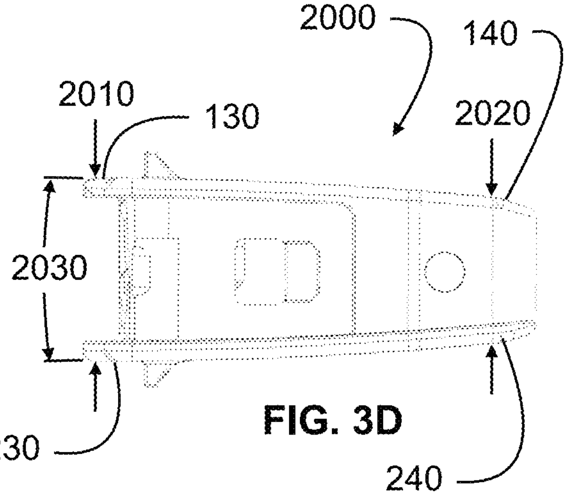
Figure 4A:
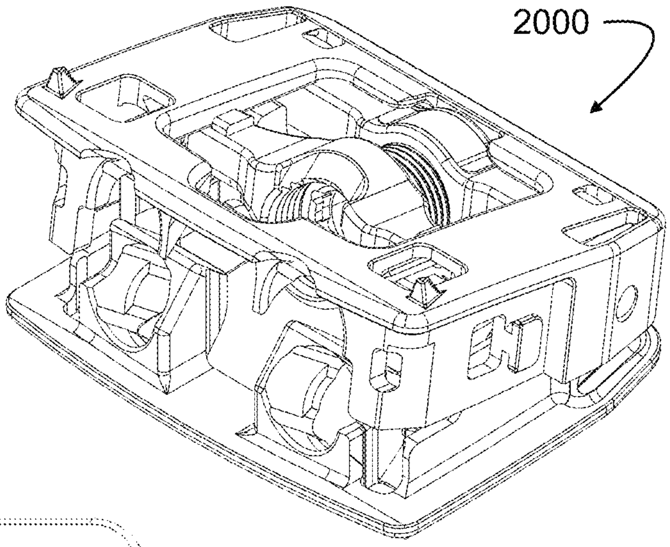
FIGS. 4A, 4B, 4C and 4D are perspective, top, front and side views of the expandable intervertebral implant of FIG. 1 in an expanded configuration.
Figure 4B:
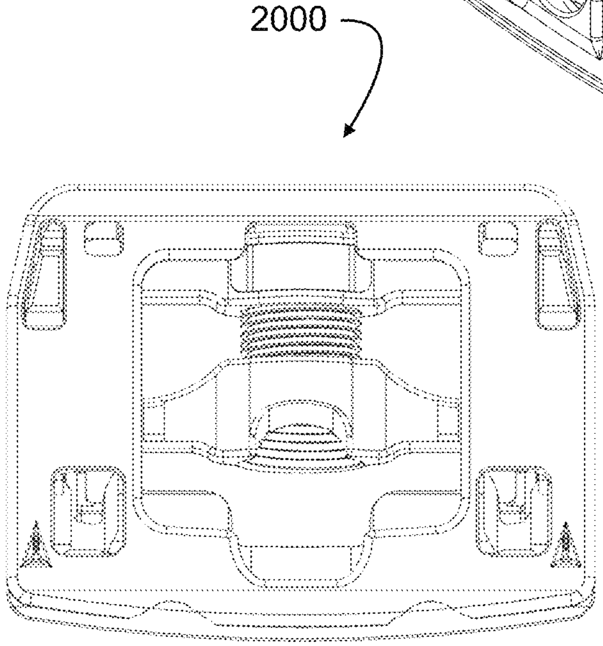
Figure 4C:
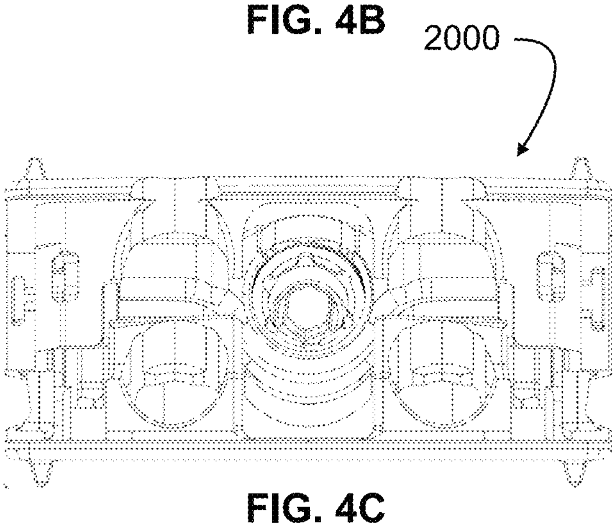
Figure 4D:
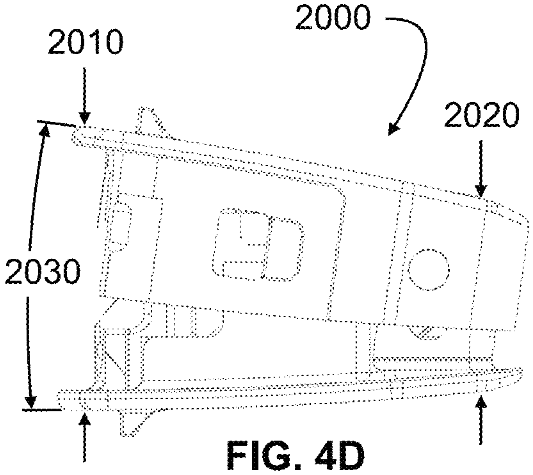

FIG. 1 is a perspective view of an expandable intervertebral implant 2000 in a collapsed configuration according to an embodiment of the present disclosure. FIG. 2 is a perspective view of the expandable intervertebral implant of FIG. 1 in an expanded configuration. In some embodiments, the expandable intervertebral implant 2000 may be configured to be implanted within a spinal disc space following a discectomy procedure during an anterior lumbar interbody fusion (ALIF) procedure. The expandable intervertebral implant 2000 may be implanted between a superior vertebra and an inferior vertebra to support fusion of the vertebral bodies. The expandable intervertebral implant 2000 may be configured to include a superior endplate 100 and an inferior endplate 200. The superior endplate 100 may include a superior anterior portion 130 and a superior posterior portion 140. The inferior endplate 200 may include an inferior anterior portion 230 and an inferior posterior portion 240.

The expandable intervertebral implant 2000 may include a superior endplate 100 configured to engage a superior vertebra; an inferior endplate 200 configured to engage an inferior vertebra and spaced apart from the superior endplate 100 by a gap, a height slider 400 moveable along an anterior-posterior direction to urge linear expansion of the gap, and an angulation slider 700 moveable along an anterior-posterior direction, to urge angular expansion of the gap. The linear expansion may be activated by engaging one or more pairs of angled surfaces. The angular expansion may be activated by a rotation and/or translation of a cam mechanism.

FIGS. 3A, 3B, 3C and 3D are perspective, top, front and side views of the expandable intervertebral implant 2000 in a collapsed configuration. The expandable intervertebral implant 2000 may have an anterior height 2010 and a posterior height 2020. The anterior height 2010 may be the distance, in a superior-inferior plane, between the superior anterior portion 130 and the inferior anterior portion 230. The posterior height 2020 may be the distance, in a superior-inferior plane, between the superior posterior portion 140 and the inferior posterior portion 240.

The expandable intervertebral implant 2000 may be configured to include a collapsed (un-expanded) configuration and one or more expanded configurations. In the collapsed configuration, the anterior height 2010 may be at a minimum of an anterior travel range and the posterior height 2020 may be at a minimum of a posterior travel range. Additionally, the expandable intervertebral implant 2000 may be configured for multiple size variations whereby the anterior height 2010 may range from 8 mm to 20 mm in the collapsed configuration. The expandable intervertebral implant 2000 may include an implant angle 2030. The expandable intervertebral implant 2000 may be configured for multiple implant angle 2030 variations ranging from 0° to 20° in the collapsed configuration.

The expandable intervertebral implant 2000 may be configured to be placed into a disc space in a collapsed configuration and expanded in-situ to restore an anatomical intervertebral disc height and/or an angle between the superior vertebra and the inferior vertebra. The expandable intervertebral implant 2000 may be configured to expand in height so that the anterior height 2010 and the posterior height 2020 increase at generally the same rate as each other during the expansion process. The expandable intervertebral implant 2000 may further be configured to expand at an angle whereby the anterior height 2010 is increased and the posterior height 2020 remains generally unchanged.

In some embodiments, the expandable intervertebral implant 2000 may be configured so that a right side of the expandable intervertebral implant 2000 and a left side of the expandable intervertebral implant 2000 may be expanded independently of each other in a medial-lateral plane. Additionally, or alternatively, the expandable intervertebral implant 2000 may be configured so that the height expansion of the expandable intervertebral implant 2000 may be independent of the angular expansion of the expandable intervertebral implant 2000. Additionally, or alternatively, the actuation mechanism for angular expansion may be independent of the actuation mechanism for linear expansion.

The expandable intervertebral implant 2000 may be configured so that the height expansion, whereby the anterior height 2010 and the posterior height 2020 increase at generally the same rate as each other during the expansion process, may be actuated by a first means, and the angular expansion, whereby the anterior height 2010 is increased and the posterior height remains generally unchanged, may be actuated by a second means. In some embodiments the first means of actuation and the second means of actuation are distinct and may be engaged independently of each other. The first means of actuation and the second means of actuation may be engaged in any sequence. The first means of actuation may include a first threaded mechanism. The second means of actuation may include a second threaded mechanism.

FIGS. 4A, 4B, 4C and 4D are perspective, top, front and side views of the expandable intervertebral implant 2000 in an expanded configuration. The implant angle 2030 of the expandable intervertebral implant 2000 may be increased through angular expansion to generally match the lordotic angle of a superior vertebra and an inferior vertebra. The expandable intervertebral implant 2000 may be configured wherein angular expansion increases the anterior height 2010 without generally increasing the posterior height 2020. In some embodiments, the expandable intervertebral implant 2000 may be configured for a posterior lumbar interbody fusion (PLIF) procedure, wherein angular expansion may increase the posterior height 2020 without generally increasing the anterior height 2010. The range of angular expansion may be between 0° and 15°.

The height of the expandable intervertebral implant 2000 may be increased through height expansion. The expandable intervertebral implant 2000 may be configured wherein height expansion increases both the anterior height 2010 and the posterior height 2020 by generally equal amounts. The range of height expansion may be between 0 mm and 8 mm.

Figure 5:
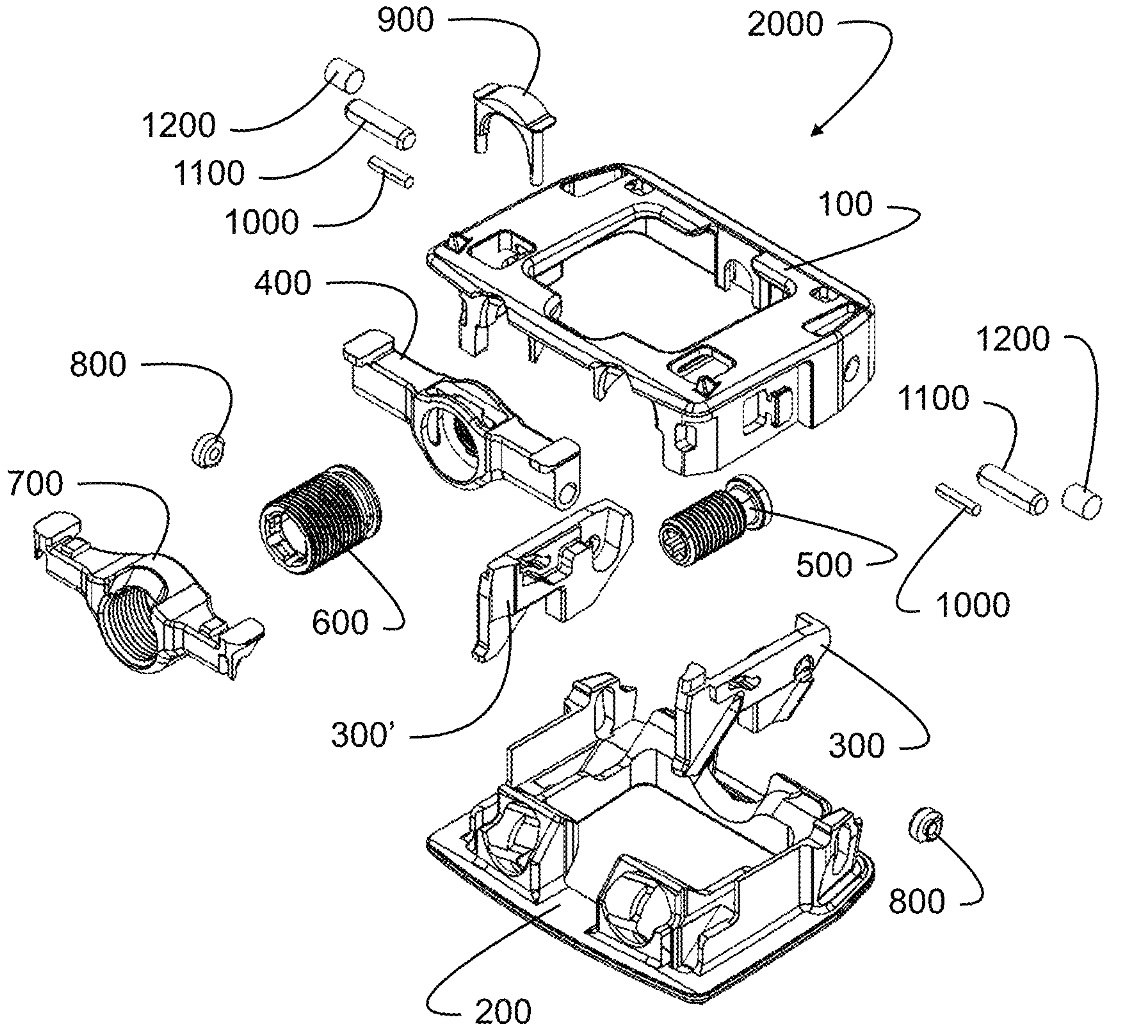
FIG. 5 is a perspective exploded view of the expandable intervertebral implant of FIG. 1.
Figure 6A:
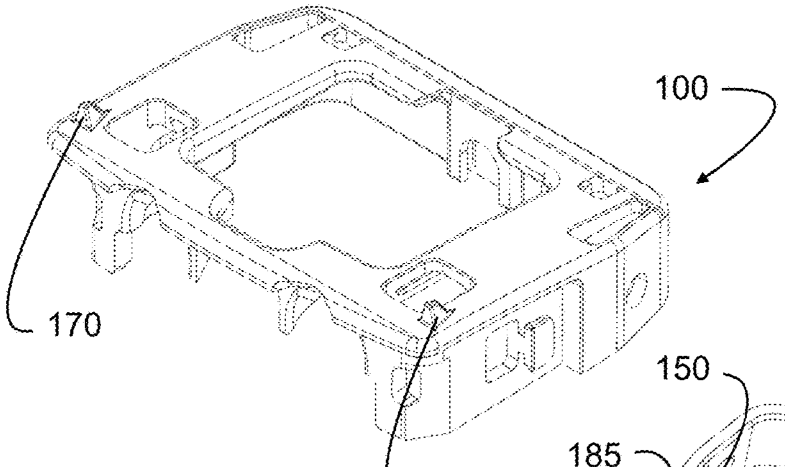
FIGS. 6A, 6B, 6C, 6D, and 6E are perspective, bottom perspective, top, front and side views of a superior endplate of the expandable intervertebral implant of FIG. 1 according to an embodiment of the present disclosure.
Figure 6B:
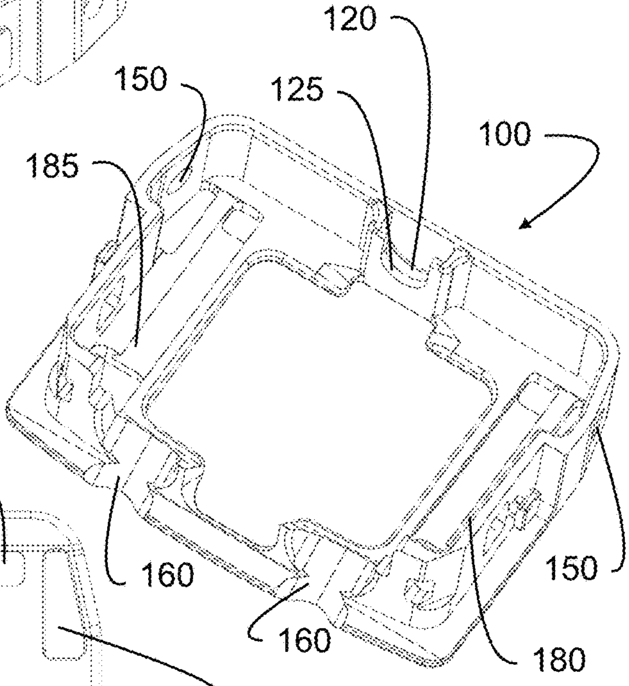
Figure 6C:
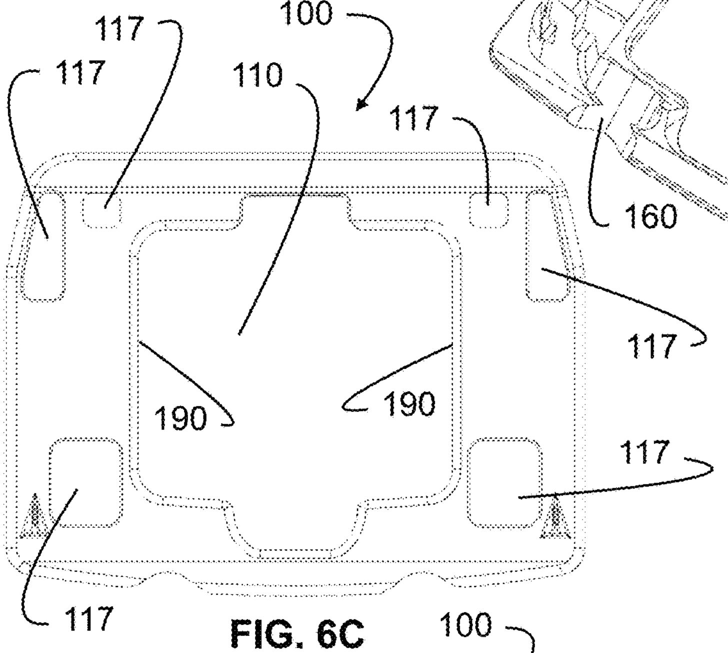
Figure 6D:
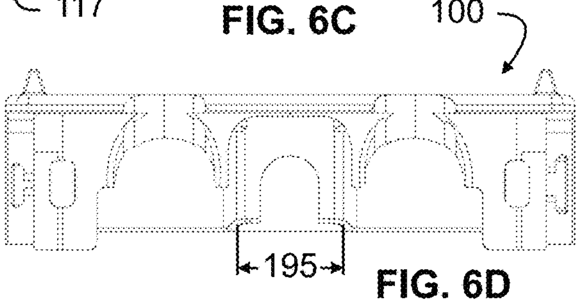
Figure 6E:
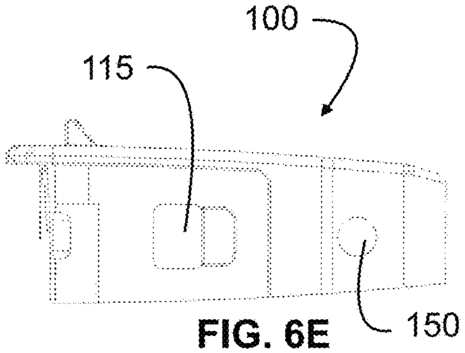
Figure 7A:
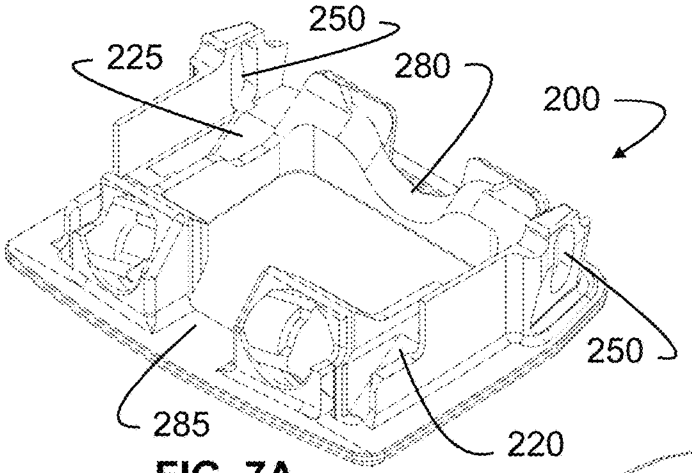
FIGS. 7A, 7B, 7C, 7D, and 7E are perspective, bottom perspective, top, front and side views of an inferior endplate of the expandable intervertebral implant of FIG. 1 according to an embodiment of the present disclosure.
Figure 7B:
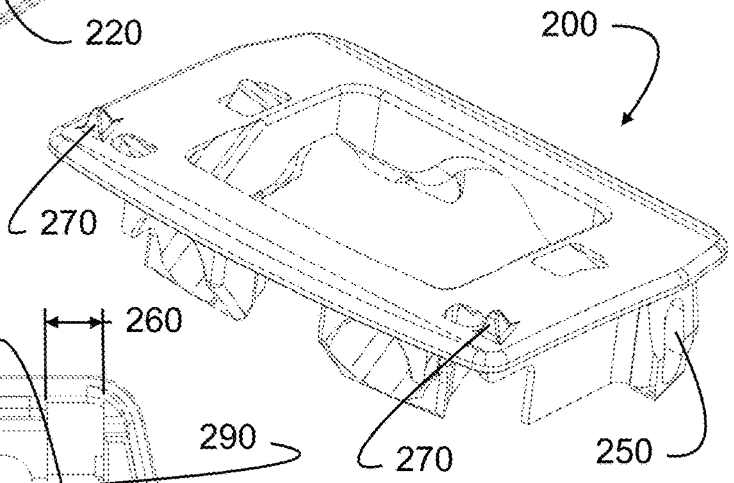
Figure 7C:
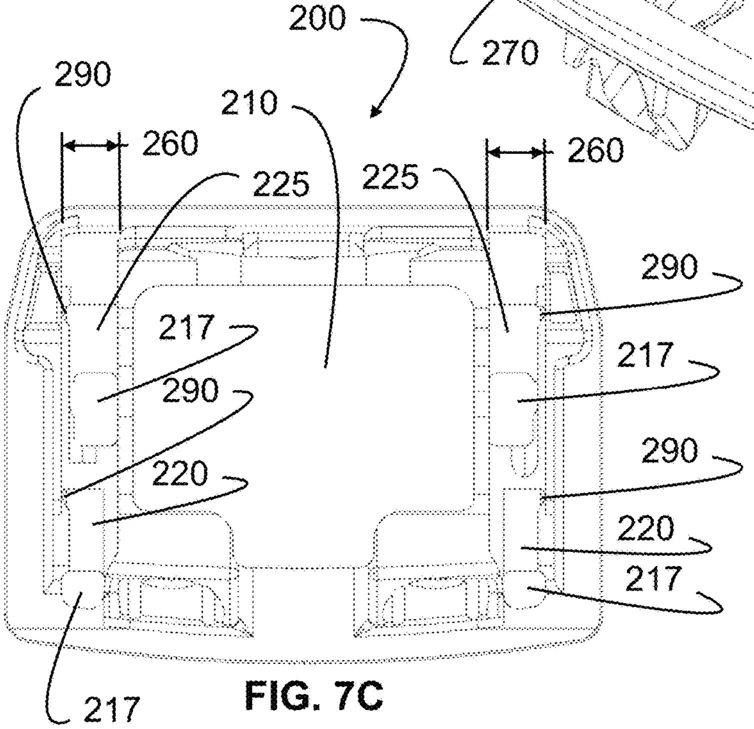
Figure 7D:
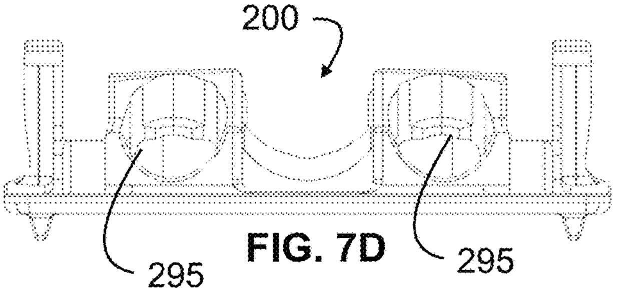
Figure 7E:
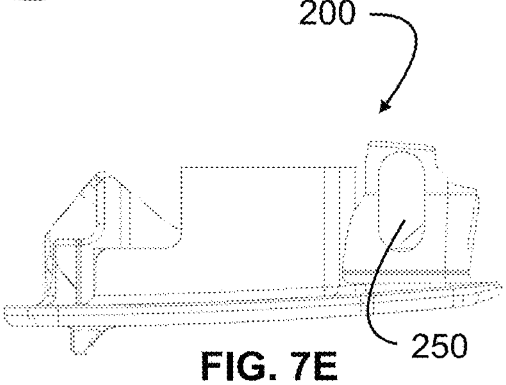
Figure 8A:
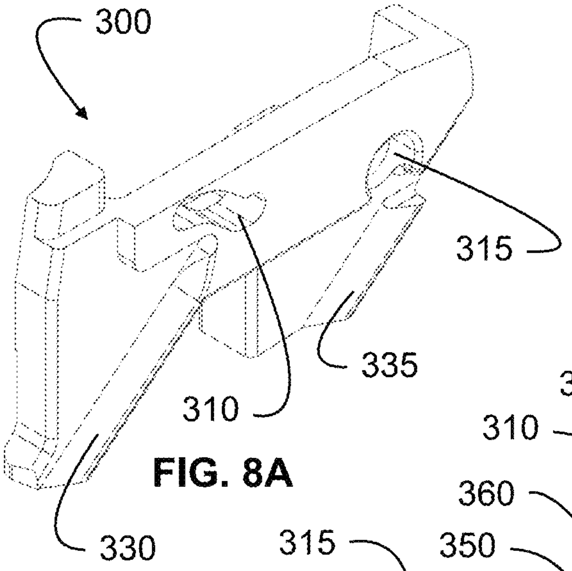
FIGS. 8A, 8B, 8C, and 8D are perspective, left side, right side, and front views of a height saddle of the expandable intervertebral implant of FIG. 1 according to an embodiment of the present disclosure.
Figure 8B:
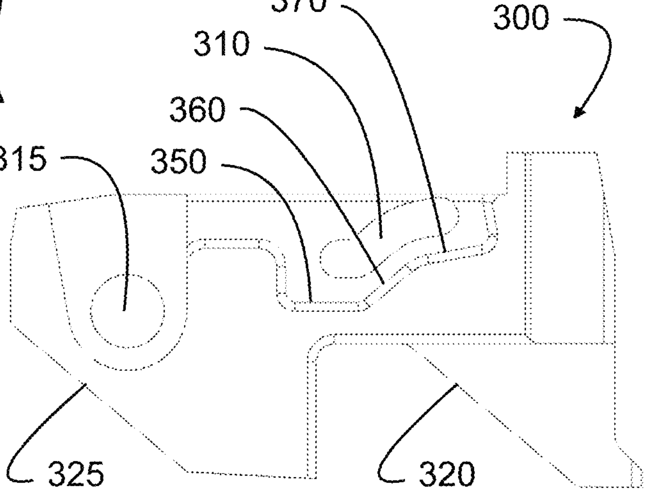
Figure 8D:
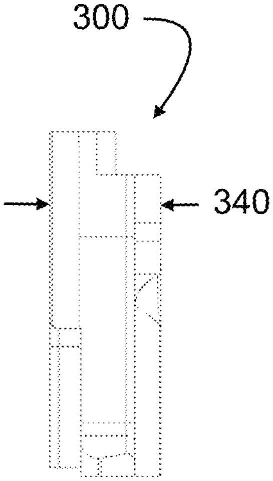
Figure 8C:
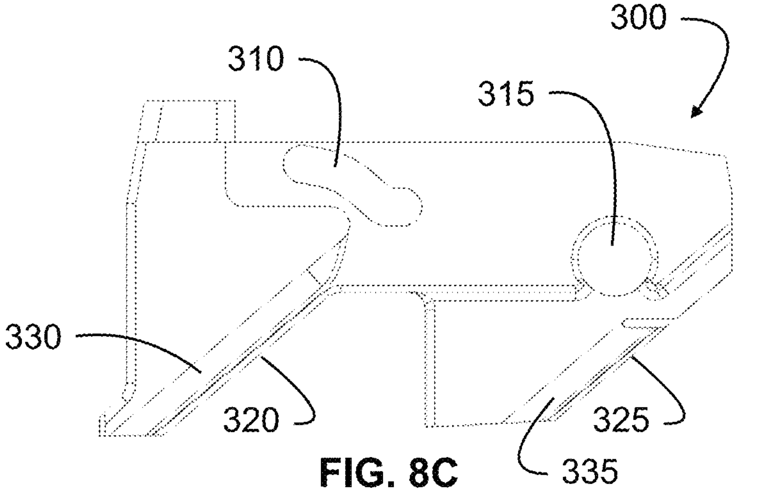
Figure 9A:
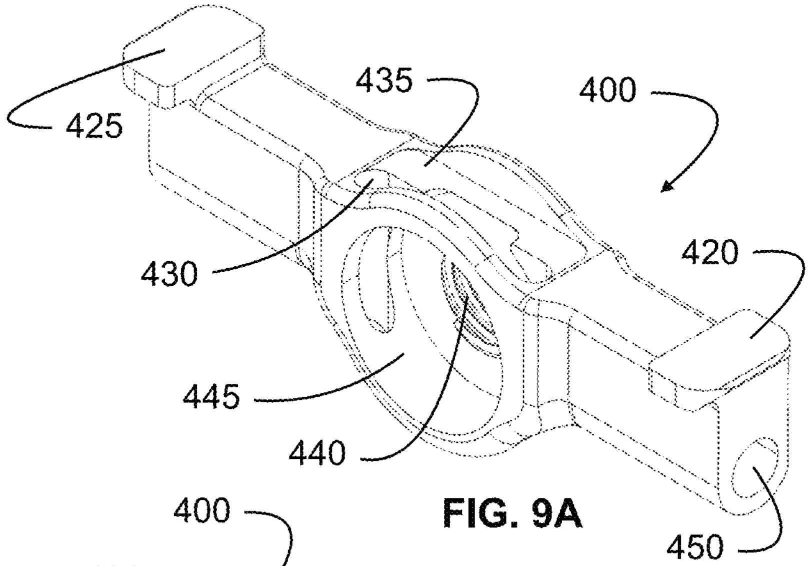
FIGS. 9A, 9B, 9C, and 9D are perspective, top, front, and side views of a height slider of the expandable intervertebral implant of FIG. 1 according to an embodiment of the present disclosure.
Figure 9B:
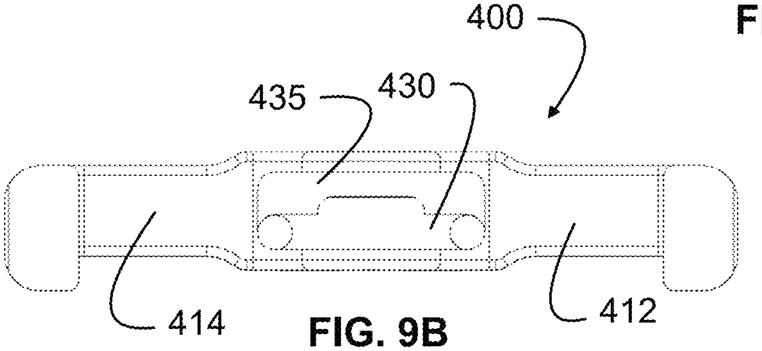
Figure 9C:
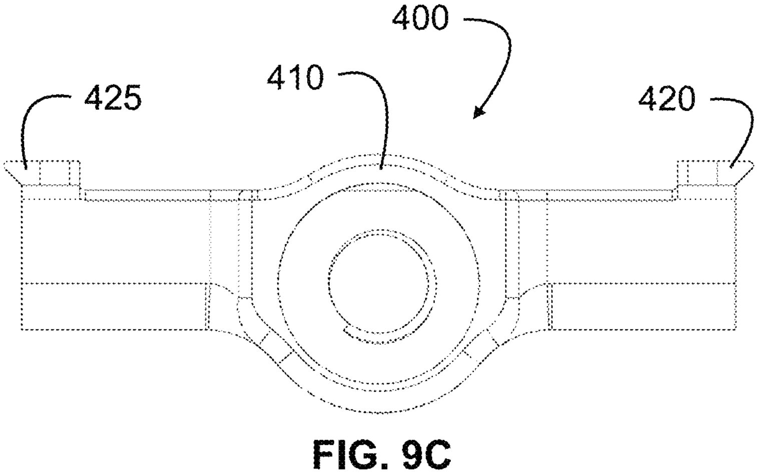
Figure 9D:
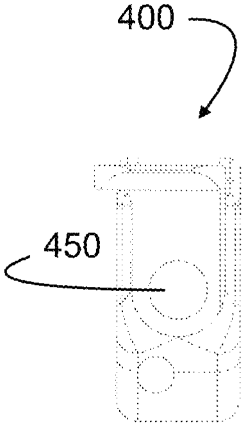

FIG. 5 is a perspective exploded view of the expandable intervertebral implant 2000. The expandable intervertebral implant 2000 may include a superior endplate 100, an inferior endplate 200, a height saddle 300, a mirror image height saddle 300', a height slider 400, a height screw 500, an angulation screw 600, an angulation slider 700, one or more angulation cams 800, an angulation screw clip 900, one or more cam pins 1000, one or more slider pins 1100, and one or more endplate pins 1200.

FIGS. 6A, 6B, 6C, 6D, and 6E are perspective, bottom perspective, top, front and side views of a superior endplate 100 of the expandable intervertebral implant 2000 according to an embodiment of the present disclosure. The superior endplate 100 may be configured to engage a superior vertebra. The superior endplate 100 may include a central aperture 110, and a plurality of peripheral apertures 117 to allow bone growth between a superior vertebra and an inferior vertebra through the expandable intervertebral implant 2000.

The superior endplate 100 may further include a plurality of side apertures 115. The superior endplate 100 may be configured to receive bone graft material within the central aperture 110 to facilitate bone ingrowth.

The superior endplate 100 may also include a pocket 120 and an opening 125. The pocket 120 and the opening 125 may be located at the posterior portion of the superior endplate 100. The pocket 120 and the opening 125 may be configured to rotatably receive the height screw 500.

The superior endplate 100 may further include one or more pin apertures 150 configured to receive one or more endplate pins 1200. The one or more endplate pins 1200 may also be received within one or more pin apertures 250 of the inferior endplate 200. The one or more endplate pins 1200 may allow rotation of the superior endplate 100 relative to the inferior end plate whereby the axis of rotation may be colinear with a longitudinal axis of the one or more endplate pins 1200. Additionally, the one or more endplate pins 1200 may be configured to translate along the length of the one or more pin apertures 250 as the height of the expandable intervertebral implant 2000 is increased.

Figure 16:
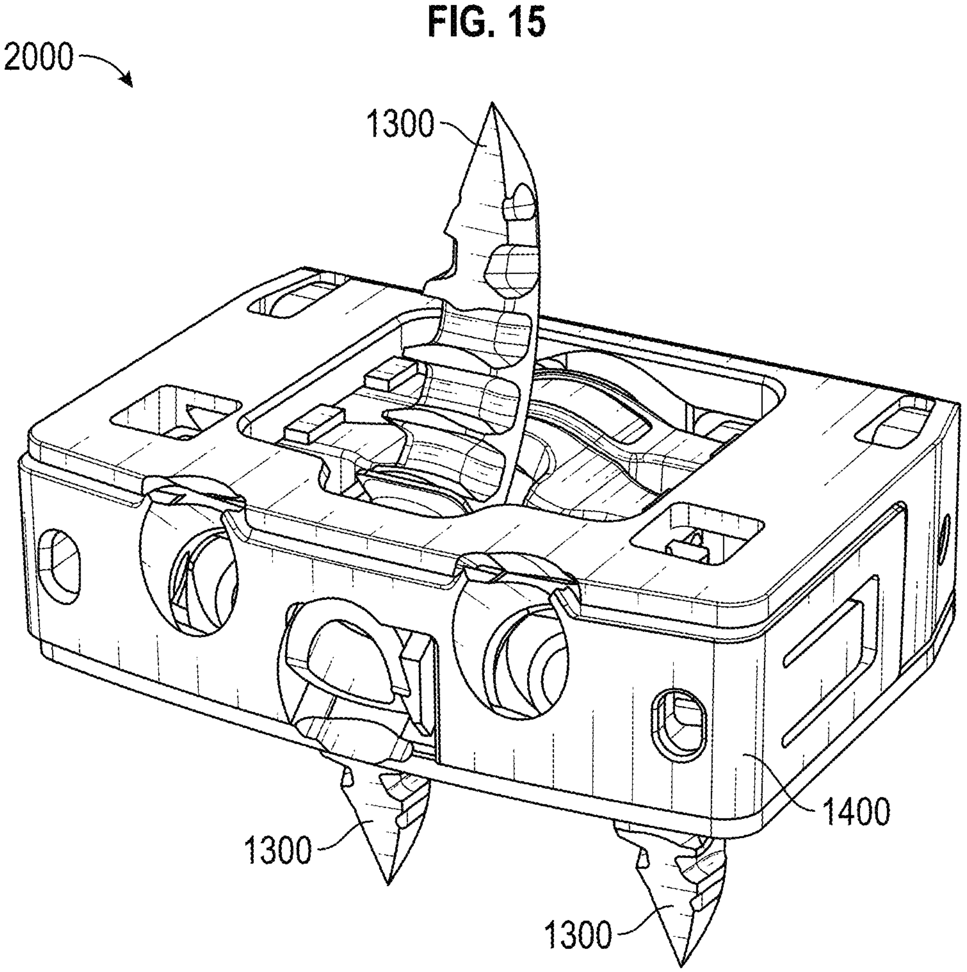
FIG. 16 is a perspective view of the expandable intervertebal implant of FIG. 1 assembled with a plate and fasteners according to an embodiment of the present disclosure.

The superior endplate 100 may further include one or more fastener channels 160 configured to allow passage of a fastener 1300 (as shown in FIG. 16) through the anterior portion of the expandable intervertebral implant 2000 and into an inferior vertebra. The superior endplate 100 may also include one or more fins 170 located on the superior anterior portion 130. The one or more fins 170 may be configured to engage the superior vertebra and may prevent expulsion, subsidence and/or migration of the expandable intervertebral implant 2000 from an intervertebral space. Additionally, or alternatively, the one or more fins 170 may be located on the superior posterior portion 140. Additionally, or alternatively, the one or more fins 170 may be located on a superior surface of the superior endplate 100.

The superior endplate 100 may include a first channel 180 and a second channel 185. The first channel 180 and the second channel 185 may be configured to slidably receive the height slider 400 and/or the angulation slider 700. The first channel 180 and the second channel 185 may each be configured with an undercut portion along one or more sides along the length of the first channel 180 and/or the second channel 185. For example, the first channel 180 and the second channel 185 may be configured with a partial dovetail profile and/or a full dovetail profile.

The first channel 180 and the second channel 185 may be configured so that the height slider 400 and/or the angulation slider 700 are slidably captive relative to the first channel 180 and/or the second channel 185. The height slider 400 and/or the angulation slider 700 may move with the superior endplate 100 during linear expansion and/or angular expansion of the expandable intervertebral implant 2000. Additionally, or alternatively, the height slider 400 and/or the angulation slider 700 may move within the first channel 180 and/or the second channel 185 during linear expansion and/or angular expansion of the expandable intervertebral implant 2000.

As used herein, "captive relative to" refers to a first component that is directly coupled with a second component such that, during movement of either component, the two components remain directly coupled. Additionally, the two components may rotate relative to each other and/or translate relative to each other while remaining directly coupled.

The superior endplate 100 may have a plurality of aperture side walls 190 at the edges of the central aperture 110. The plurality of aperture side walls 190 may be generally parallel to the first channel 180 and the second channel 185. The superior endplate 100 may also include a boss width 195. The boss width 195 may be greater than the pocket 120 and the opening 125.

FIGS. 7A, 7B, 7C, 7D, and 7E are perspective, bottom perspective, top, front and side views of an inferior endplate 200 of the expandable intervertebral implant 2000 according to an embodiment of the present disclosure. The inferior endplate 200 may be configured to engage an inferior vertebra. The inferior endplate 200 may include a central aperture 210, and a plurality of peripheral apertures 217 to allow bone growth between a superior vertebra and an inferior vertebra through the expandable intervertebral implant 2000. The inferior endplate 200 may be configured to receive bone graft material within the central aperture 210 to facilitate bone ingrowth.

The inferior endplate 200 may include one or more first angled portions 220 and one or more second angled portions 225. The one or more first angled portions 220 may be configured to slidably engage one or more third angled portions 320 of the height saddle 300. The one or more second angled portions 225 may be configured to slidably engage one or more fourth angled portions 325 of the height saddle 300. The one or more first angled portions 220 and the one or more second angled portions 225 may be configured so that a force applied in a posterior direction from the one or more third angled portions 320 and/or one or more fourth angled portions 325 may result in translation of the superior endplate 100.

The one or more first angled portions 220 and the one or more second angled portions 225 may each include one or more side grooves 290. The one or more side grooves 290 may be configured as an undercut portion along one or more sides along the length of the one or more first angled portions 220 and/or the one or more second angled portions 225. For example, the one or more side grooves 290 may be configured with a partial dovetail profile and/or a full dovetail profile.

The first angled portion 220 and the second angled portion 225 may be included in one or more saddle channels 260. The one or more saddle channels 260 may slidably receive one or more height saddles 300 and/or one or more height saddles 300' and may guide movement of the one or more height saddles 300 and/or one or more height saddles 300' in a generally anterior-posterior direction.

The inferior endplate 200 may also include one or more fins 270 located on the inferior anterior portion 230. The one or more fins 270 may be configured to engage the superior vertebra and may prevent expulsion, subsidence and/or migration of the expandable intervertebral implant 2000 from an intervertebral space. Additionally, or alternatively, the one or more fins 270 may be located on the inferior posterior portion 240. Additionally, or alternatively, the one or more fins 270 may be located on an inferior surface of the inferior endplate 200.

The inferior endplate 200 may further include a posterior opening 280 and an anterior opening 285. The posterior opening 280 may be configured so that the height screw 500 does not impact the inferior endplate 200 over the entire range of travel of the height screw 500 when the expandable intervertebral implant 2000 is in the collapsed configuration, the one or more expanded configurations and/or transitioning between the collapsed configuration and the one or more expanded configurations. The anterior opening 285 may be configured to allow a driver to engage the height screw 500 and/or the angulation screw 600 through an anterior portion of the inferior endplate 200 when the expandable intervertebral implant 2000 is in the collapsed configuration, the one or more expanded configurations and/or transitioning between the collapsed configuration and the one or more expanded configurations.

The inferior endplate 200 may further include one or more fastener apertures 295 configured to allow passage of a fastener 1300 (as shown in FIG. 16) through the anterior portion of the expandable intervertebral implant 2000 and into an inferior vertebra.

FIGS. 8A, 8B, 8C, and 8D are perspective, left side, right side, and front views of a height saddle 300 of the expandable intervertebral implant 2000 according to an embodiment of the present disclosure. The expandable intervertebral implant 2000 may include a height saddle 300 and a height saddle 300' wherein the height saddle 300' may be a complete mirror image of the height saddle 300. All features subsequently described for the height saddle 300 may also be present on the height saddle 300'.

The height saddle 300 may be configured to translate anterior-posterior motion into inferior-superior motion. More specifically, as the height saddle 300 is urged in a posterior direction by the height slider 400, which may be actuated by the height screw 500, the height saddle 300 may slidably engage one or more angled surfaces of the inferior endplate 200 resulting in movement of the height saddle 300 in a superior direction thereby urging the superior endplate 100 in a superior direction.

The height saddle 300 may include one or more third angled portions 320 and one or more fourth angled portions 325. The one or more third angled portions 320 may be configured to slidably engage one or more first angled portions 220 of the inferior endplate 200. The one or more fourth angled portions 325 may be configured to slidably engage one or more second angled portions 225 of the inferior endplate 200. The one or more third angled portions 320 and/or the one or more fourth angled portions 325 may be configured so that a force applied in a posterior direction from height slider 400 may result in translation of the superior endplate 100.

The one or more third angled portions 320 may include one or more first engagement portions 330. The one or more fourth angled portions 325 may include one or more second engagement portions 335. The one or more first engagement portions 330 and/or the one or more second engagement portions 335 may be configured to slidably engage the one or more side grooves 290 of the inferior endplate 200.

The height saddle 300 may have a saddle width 340. The saddle width 340 may be less than or equal to the width of the one or more saddle channels 260 of the inferior endplate 200. The one or more first engagement portions 330 and/or the one or more second engagement portions 335 may be configured so that the height saddle 300 may be slidably captive relative to the one or more saddle channels 260 of the inferior endplate 200.

The height saddle 300 may include a cam slot 310 and a pin aperture 315. The cam slot 310 may be configured to receive a cam pin 1000. The pin aperture 315 may be configured to receive a slider pin 1100. The height saddle 300 may also include a first cam engagement surface 350, a second cam engagement surface 360, and a third cam engagement surface 370. The cam slot 310 in conjunction with the cam pin 1000 may guide the translation and/or rotation of an angulation cam 800 along the first cam engagement surface 350, the second cam engagement surface 360, and the third cam engagement surface 370.

FIGS. 9A, 9B, 9C, and 9D are perspective, top, front, and side views of a height slider 400 of the expandable intervertebral implant 2000 according to an embodiment of the present disclosure. The height slider 400 may be configured to slidably engage the superior endplate 100. The height slider 400 may further be configured to translate rotational motion of the height screw 500 into linear motion of the height slider 400 with respect to the superior endplate 100. Movement of the height slider 400 may result in comparable movement of the angulation slider 700.

The height slider 400 may include a central portion 410, a first arm 412, and a second arm 414. The central portion 410 may include a first pocket 430, a second pocket 435, an inside diameter 445, and an internal thread 440. The internal thread 440 may be configured to threadably receive the height screw 500. The internal thread 440 may include a left-hand thread having a thread pitch and a pitch diameter compatible with the external thread 510 of the height screw 500.

The inside diameter 445 may be configured to rotatably receive the angulation screw 600. The first pocket 430 and the second pocket 435 may be configured to receive the angulation screw clip 900. More specifically, the first pocket 430 may receive the one or more legs 910 and the first locating feature 920 of the angulation screw clip 900. The second pocket 435 may receive the second locating feature 930 of the angulation screw clip 900. The height slider 400, the angulation screw 600, and the angulation screw clip 900 may be configured so that the angulation screw 600 is rotatably captive relative to the inside diameter 445.

The first arm 412 may include a first engagement portion 420 and the second arm 414 may include a second engagement portion 425. The first engagement portion 420 may be configured to slidably engage the first channel 180 of the superior endplate 100. The second engagement portion 425 may be configured to slidably engage the second channel 185 of the superior endplate 100. The first engagement portion 420 and the second engagement portion 425 may each be configured with an undercut portion configured to slidably engage a complimentary undercut portion along one or more sides along the length of the first channel 180 and/or the second channel 185. For example, the first channel 180 and the second channel 185 may be configured with a partial female dovetail profile or a full female dovetail profile and the first engagement portion 420 and the second engagement portion 425 may each include a complimentary partial male dovetail profile or a full male dovetail profile.

The first arm 412 and the second arm 414 may each include a pin aperture 450. The pin aperture 450 may be configured to receive a slider pin 1100. The slider pin 1100 may allow rotation of the height slider 400 with respect to the height saddle 300 whereby the axis of rotation may be colinear with a longitudinal axis of the slider pin 1100 and the pin aperture 450.

Figure 10A:
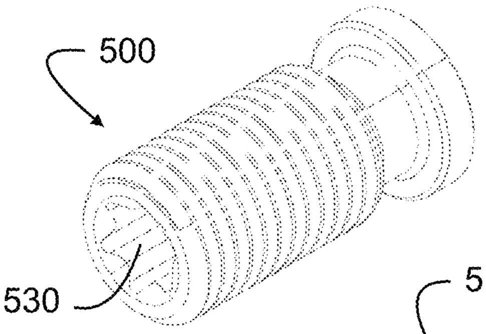
FIGS. 10A, 10B, and 10C are perspective, front, and side views of a height screw of the expandable intervertebral implant of FIG. 1 according to an embodiment of the present disclosure.
Figure 10B:
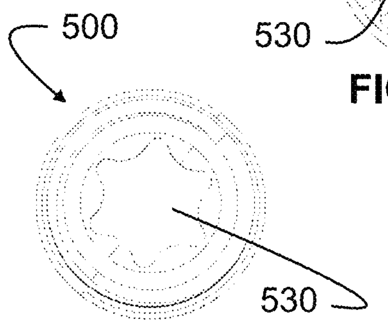
Figure 10C:
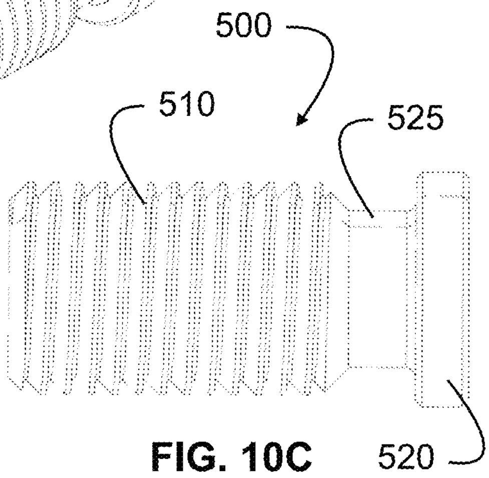

FIGS. 10A, 10B, and 10C are perspective, front, and side views of a height screw 500 of the expandable intervertebral implant 2000 according to an embodiment of the present disclosure. The height screw 500 may be a component of an actuation mechanism configured to translate rotational motion into linear motion. The height screw 500 may include a head 520 and a neck 525. The head 520 may be rotatably captive relative to the pocket 120 of the superior endplate 100 and the neck 525 may rotatably engage the opening 125 of the superior endplate 100, thereby restricting linear motion of the height screw 500 with respect to the superior endplate 100.

The height screw 500 may have an external thread 510 that may be configured to threadably engage the internal thread 440 of the height slider 400. The external thread 510 may include a left-hand thread having a thread pitch and a pitch diameter compatible with the internal thread 440 of the height slider 400.

The height screw 500 may also include a drive feature 530. The drive feature 530 may have a hexalobe geometry or the like; this geometry may match that of a tip portion of a driver (not shown) that may impart torque to the height screw 500 through rotation of the driver. The drive feature 530 may have a hex, a hexalobe, a square or other non-circular profile known in the art. In alternative embodiments, the drive feature 530 may have a different geometry or may be replaced by one or more positive features such as a boss or any other driver tip geometry known in the art.

Figure 11A:
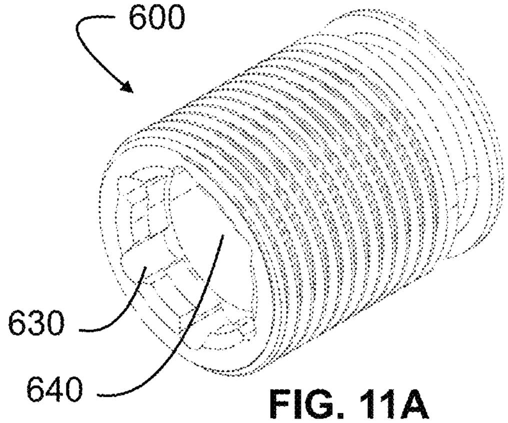
FIGS. 11A, 11B, and 11C are perspective, front, and side views of an angulation screw of the expandable intervertebral implant of FIG. 1 according to an embodiment of the present disclosure.
Figure 11B:
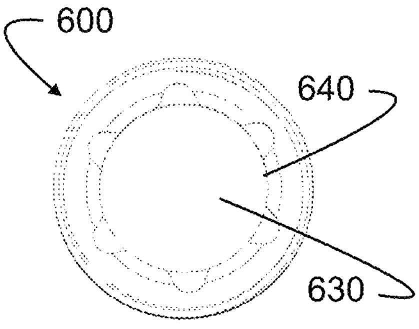
Figure 11C:
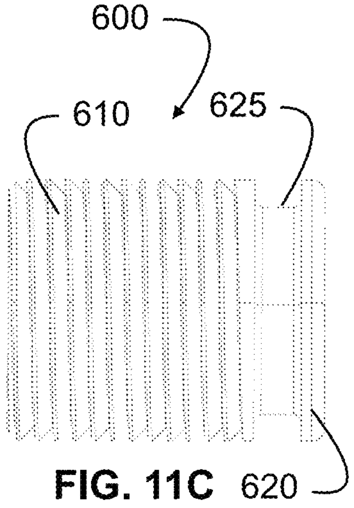
Figure 12A:
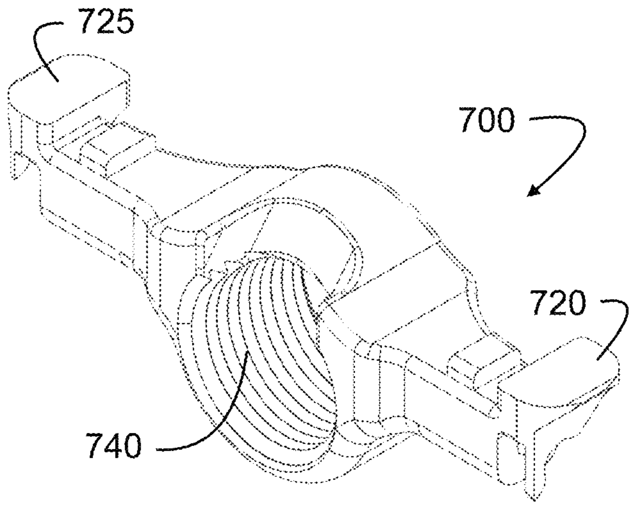
FIGS. 12A, 12B, 12C, and 12D are perspective, top, front, and side views of an angulation slider of the expandable intervertebral implant of FIG. 1 according to an embodiment of the present disclosure.
Figure 12B:
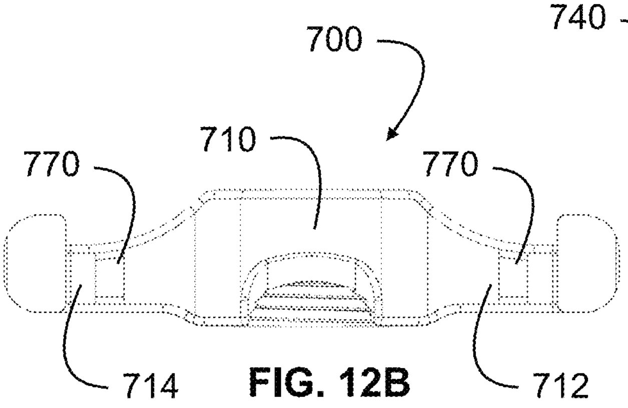
Figure 12C:
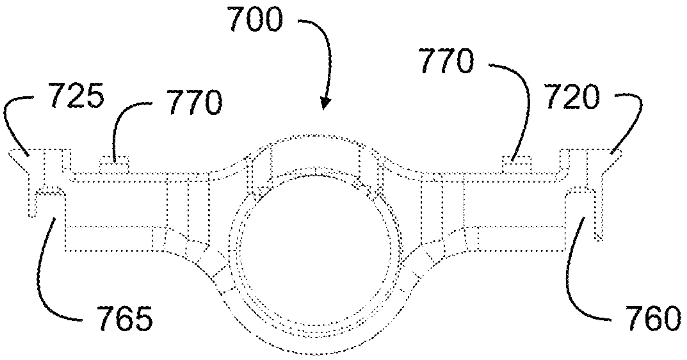
Figure 12D:
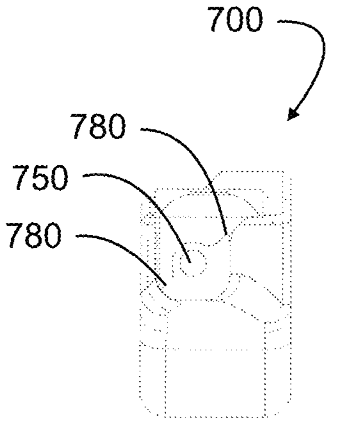

FIGS. 11A, 11B, and 11C are perspective, front, and side views of an angulation screw 600 of the expandable intervertebral implant 2000 according to an embodiment of the present disclosure. The angulation screw 600 may be a component of an actuation mechanism configured to translate rotational motion into linear motion. The angulation screw 600 may include a head 620 and a neck 625. The head 620 may be rotatably captive relative to the inside diameter 445 of the height slider 400 and the neck 625 may rotatably engage the first locating feature 920 of the angulation screw clip 900, thereby restricting linear motion of the angulation screw 600 with respect to the height slider 400.

The angulation screw 600 may have an external thread 610 that may be configured to threadably engage the internal thread 740 of the angulation slider 700. The external thread 610 may include a right-hand thread having a thread pitch and a pitch diameter compatible with the internal thread 740 of the angulation slider 700.

The angulation screw 600 may also include a drive feature 630. The drive feature 630 may have a hexalobe geometry or the like; this geometry may match that of a tip portion of a driver (not shown) that may impart torque to the angulation screw 600 through rotation of the driver. The drive feature 630 may have a hex, a hexalobe, a square or other non-circular profile known in the art.

The angulation screw 600 may also include an internal diameter 640. The internal diameter 640 may allow a driver to pass through the angulation screw 600 and engage the height screw 500. The internal diameter 640 may further allow rotation of the driver while engaged with the height screw 500 thereby imparting a torque to the height screw 500. The internal diameter 640 may be larger than a standard minor diameter of a hexalobe drive feature resulting in a modified hexalobe drive feature.

FIGS. 12A, 12B, 12C, and 12D are perspective, top, front, and side views of an angulation slider 700 of the expandable intervertebral implant 2000 according to an embodiment of the present disclosure. The angulation slider 700 may be configured to slidably engage the superior endplate 100. The angulation slider 700 may further be configured to translate rotational motion of the angulation screw 600 into linear motion of the angulation slider 700 with respect to the height slider 400. Movement of the angulation slider 700 may not result in movement of the height slider 400.

The angulation slider 700 may include a central portion 710, a first arm 712, and a second arm 714. The central portion 710 may include an internal thread 740 configured to threadably receive the angulation screw 600. The internal thread 740 may include a right-hand thread having a thread pitch and a pitch diameter compatible with the external thread 610 of the angulation screw 600.

The first arm 712 may include a first engagement portion 720 and the second arm 714 may include a second engagement portion 725. The first engagement portion 720 may be configured to slidably engage the first channel 180 of the superior endplate 100. The second engagement portion 725 may be configured to slidably engage the second channel 185 of the superior endplate 100. The first engagement portion 720 and the second engagement portion 725 may each be configured with an undercut portion configured to slidably engage a complimentary undercut portion along one or more sides along the length of the first channel 180 and/or the second channel 185. For example, the first channel 180 and the second channel 185 may be configured with a partial female dovetail profile or a full female dovetail profile and the first engagement portion 720 and the second engagement portion 725 may each include a complimentary partial male dovetail profile or a full male dovetail profile.

The first arm 712 and the second arm 714 may each include a pin aperture 750. The pin aperture 750 may be configured to receive a cam pin 1000. The cam pin 1000 may be received in the cam slot 310 of the height saddle 300. Additionally, the cam pin 1000 in conjunction with the cam slot 310 may guide the movement and/or rotation of an angulation cam 800 whereby the axis of rotation may be colinear with an axis of the cam pin 1000 and the pin aperture 750.

The first arm 712 may further include a first cam pocket 760 and the second arm 714 may further include a second cam pocket 765. The first cam pocket 760 and the second cam pocket 765 may each be configured to receive an angulation cam 800. The pin aperture 750 may extend into each of the first arm 712 and the second arm 714 so that the cam pin 1000 may allow an angulation cam 800 to be rotatably captive relative to each of the first cam pocket 760 and the second cam pocket 765.

The first arm 712 and the second arm 714 may each have a locating boss 770 and one or more cam locating surfaces 780. The locating boss 770 may be configured so that, when the first engagement portion 720 is slidably received within the first channel 180 of the superior endplate 100, the locating boss 770 is proximate the aperture side wall 190 of the superior endplate 100, thereby helping keep the angulation slider 700 aligned within the first channel 180 and the second channel 185 resulting smooth motion of the angulation slider 700 with respect to the superior endplate 100.

The one or more cam locating surfaces 780 may be configured to limit rotation of the one or more angulation cams 800. The one or more cam locating surfaces 780 may engage a first locating surface 890 and/or a second locating surface 895 of the one or more angulation cams 800.

Figure 13A:
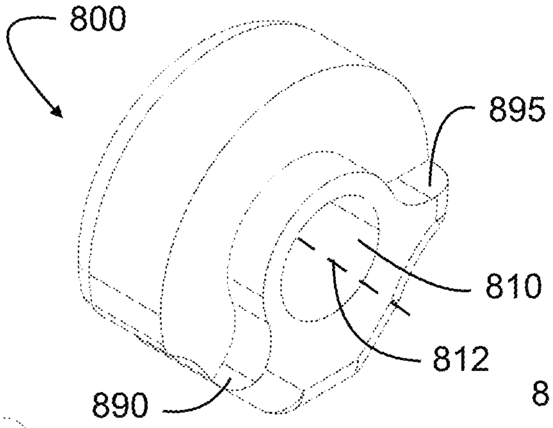
FIGS. 13A, 13B, and 13C are perspective, front, and side views of an angulation cam of the expandable intervertebral implant of FIG. 1 according to an embodiment of the present disclosure.
Figure 13B:
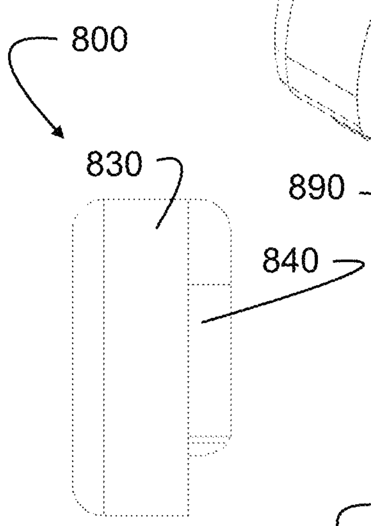
Figure 13C:
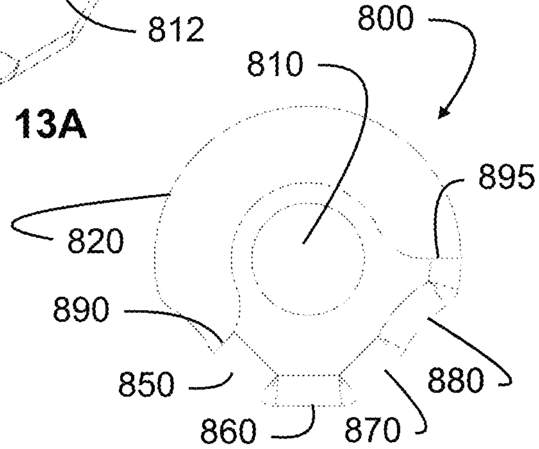

FIGS. 13A, 13B, and 13C are perspective, front, and side views of an angulation cam 800 of the expandable intervertebral implant 2000 according to an embodiment of the present disclosure. The one or more angulation cams 800 may be components of an actuation mechanism configured to translate rotational motion into angular motion. The angulation cam 800 may include a pin aperture 810 configured to receive a cam pin 1000. The angulation cam 800 may be coupled to the angulation slider 700 by the cam pin 1000.

The angulation cam 800 may further include an outside diameter 820, a body portion 830, and a locating portion 840. The outside diameter 820 and the body portion 830 may be configured to allow the angulation cam 800 to be rotatably received within the first cam pocket 760 and/or the second cam pocket 765. The pin aperture 810 may include a rotation axis 812 about which the angulation cam may rotate. The angulation cam 800 may be configured to be rotatable and translatable relative to the superior endplate 100 and the inferior endplate 200.

The locating portion 840 may include a first cam surface 850, a second cam surface 860, a third cam surface 870, a fourth cam surface 880, a first locating surface 890, and a second locating surface 895. The first cam surface 850, the second cam surface 860, the third cam surface 870, and/or the fourth cam surface 880 may engage the first cam engagement surface 350, the second cam engagement surface 360, and/or the third cam engagement surface 370 of the height saddle 300 as the expandable intervertebral implant 2000 transitions from a collapsed configuration to one or more expanded configurations. More specifically, the first cam surface 850, the second cam surface 860, the third cam surface 870, and/or the fourth cam surface 880 may engage the first cam engagement surface 350, the second cam engagement surface 360, and/or the third cam engagement surface 370 of the height saddle 300 as the angulation screw 600 is rotated and the angulation slider translates from a first position to a second position.

Figure 14A:
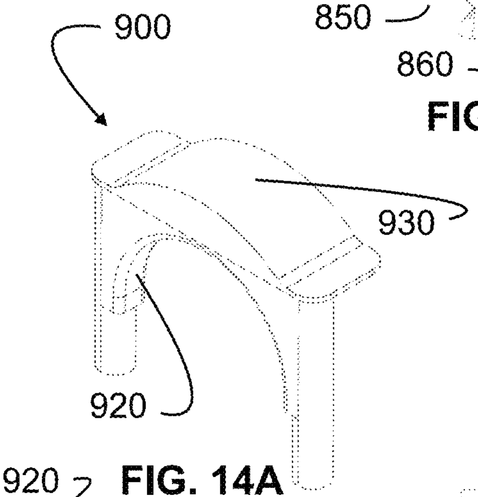
FIGS. 14A, 14B, and 14C are perspective, front, and side views of an angulation screw clip of the expandable intervertebral implant of FIG. 1 according to an embodiment of the present disclosure.
Figure 14B:
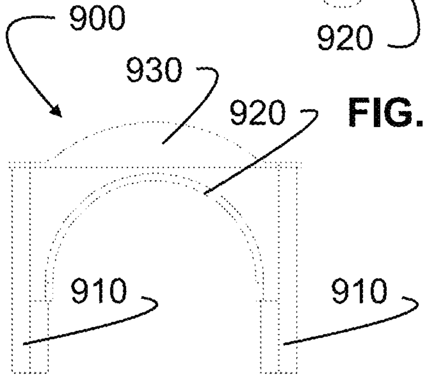
Figure 14C:
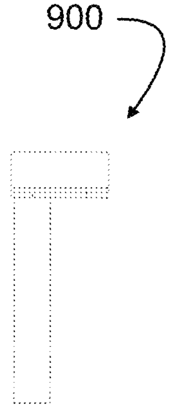

FIGS. 14A, 14B, and 14C are perspective, front, and side views of an angulation screw clip 900 of the expandable intervertebral implant 2000 according to an embodiment of the present disclosure. The angulation screw clip 900 may be configured to rotatably retain the angulation screw 600 within the height slider 400. The angulation screw clip 900 may include one or more legs 910, a first locating feature 920, and a second locating feature 930. The angulation screw clip 900 may be configured to be received within the first pocket 430 and the second pocket 435 of the height slider 400. More specifically, the one or more legs 910 and the first locating feature 920 may be received within the first pocket 430 of the height slider 400. The second locating feature 930 may be received within the second pocket 435 of the height slider 400. The height slider 400, the angulation screw 600, and the angulation screw clip 900 may be configured so that the angulation screw 600 is rotatably captive relative to the inside diameter 445 of the height slider 400.

Figure 15:
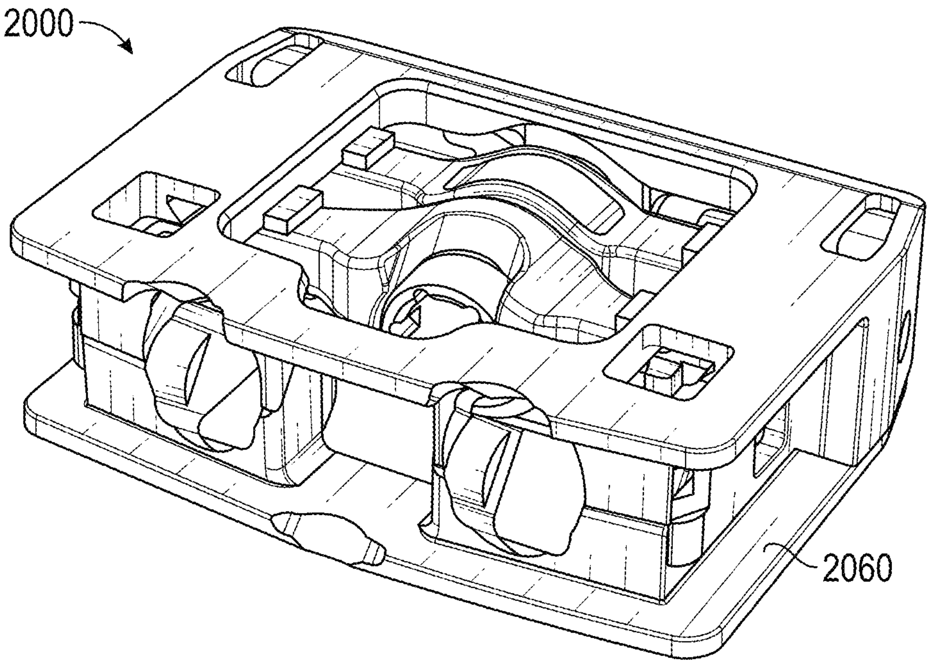
FIG. 15 is a perspective view of the expandable intervertebral implant of FIG. 1 in a collapsed configuration.

FIG. 15 is a perspective view of the expandable intervertebral implant 2000 in a collapsed configuration. FIG. 16 is a perspective view of the expandable intervertebral implant 2000 assembled with a plate 1400 and fasteners 1300 according to an embodiment of the present disclosure. The expandable intervertebral implant 2000 may include a plate receiving portion 2060. The expandable intervertebral implant 2000 may use similar fasteners, similar instruments, and/or similar methods, including the plate 1400 and the fasteners 1300, as described in U.S. Pat. No. 10,758,370 filed on Jul. 2, 2018, entitled "INTERBODY SPACER AND BONE PLATE ASSEMBLY", the disclosure of which is incorporated herein by reference in its entirety.

Figure 17A:
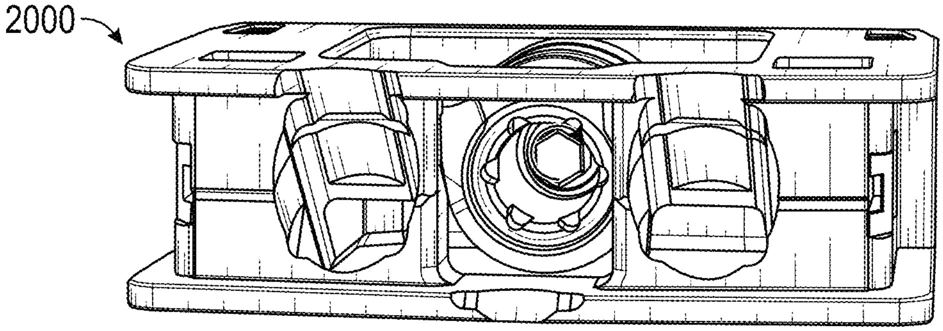
FIGS. 17A, 17B and 17C are a front perspective, side, and top perspective view of the expandable intervertebral implant of FIG. 1 showing the steps to transition from a collapsed configuration to an intermediate expanded configuration.
Figure 17B:
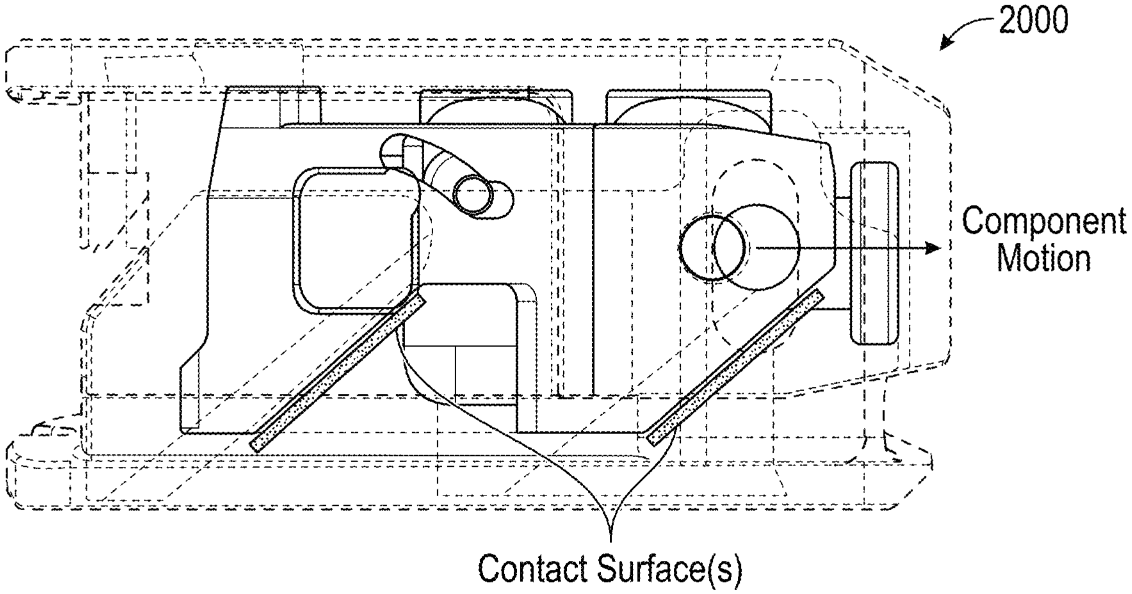
Figure 17C:
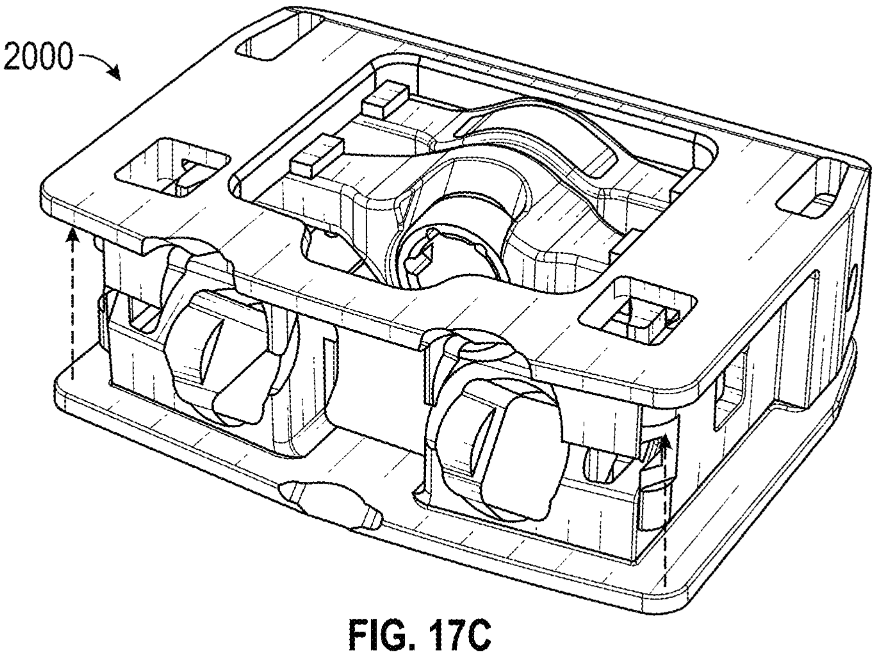

FIGS. 17A, 17B and 17C are a front perspective, side, and top perspective view of the expandable intervertebral implant 2000 showing the steps to transition from a collapsed configuration to an intermediate expanded configuration. A method for height expansion of the expandable intervertebral implant 2000 may include the following steps: engaging a first driver tool (not shown) with the drive feature 530 of the height screw 500 and rotating the first driver tool clock-wise. The clock-wise rotation of the height screw 500 may result in translation of the height slider 400 in a posterior direction. The height saddle 300 and the height saddle 300' may be linked to the height slider 400 and may also translate in a posterior direction. The height saddle 300 and the height saddle 300' may slidably engage the one or more first angled portions 220 and the one or more second angled portions 225 of the inferior endplate 200 resulting in translation of the height saddle 300 and the height saddle 300', as well as the height slider 400, the angulation slider 700, and the superior endplate 100, in a superior direction.

Figure 18A:
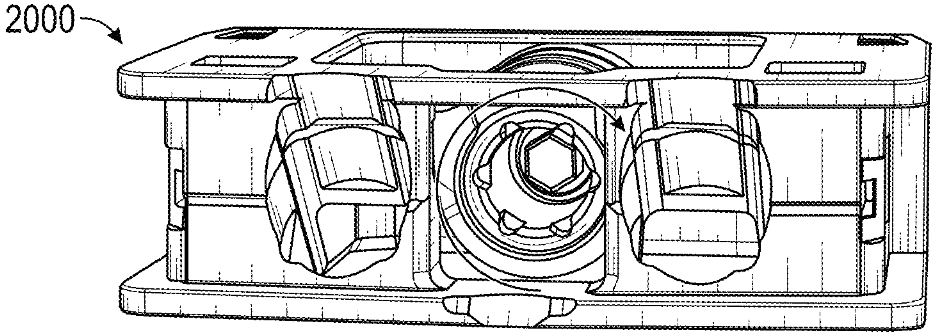
FIGS. 18A, 18B and 18C are a front perspective, top perspective, and side view of the expandable intervertebral implant of FIG. 1 showing the steps to transition from a collapsed configuration to an expanded configuration.
Figure 18B:
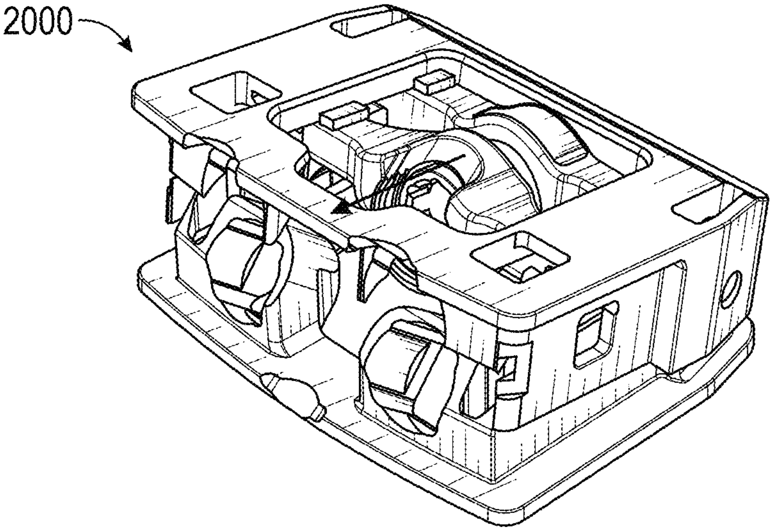
Figure 18C:
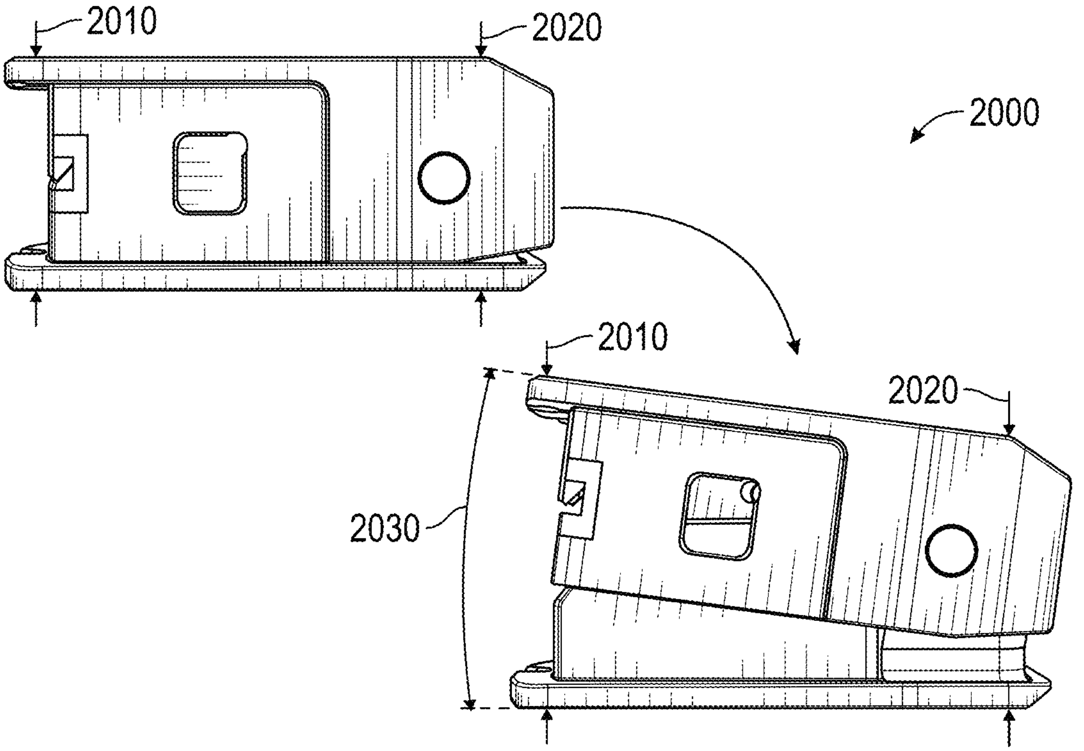

FIGS. 18A, 18B and 18C are a front perspective, top perspective, and side view of the expandable intervertebral implant 2000 showing the steps to transition from a collapsed configuration to an expanded configuration. A method for angular expansion of the expandable intervertebral implant 2000 may include the following steps: engaging a second driver tool (not shown) with the drive feature 630 of the angulation screw 600 and rotating the second driver tool clock-wise. The clock-wise rotation of the angulation screw 600 may result in translation of the angulation slider 700 in an anterior direction. The one or more angulation cams 800 may be linked to the angulation slider 700 whereby the anterior movement of the angulation slider 700 may result in the one or more angulation cams 800 translating and/or rotating while following the cam slot 310 of height saddle 300 and/or height saddle 300', resulting in movement of the angulation slider 700 in a superior direction, an increase in the anterior height 2010, and an increase in the implant angle 2030.

Figure 19A:
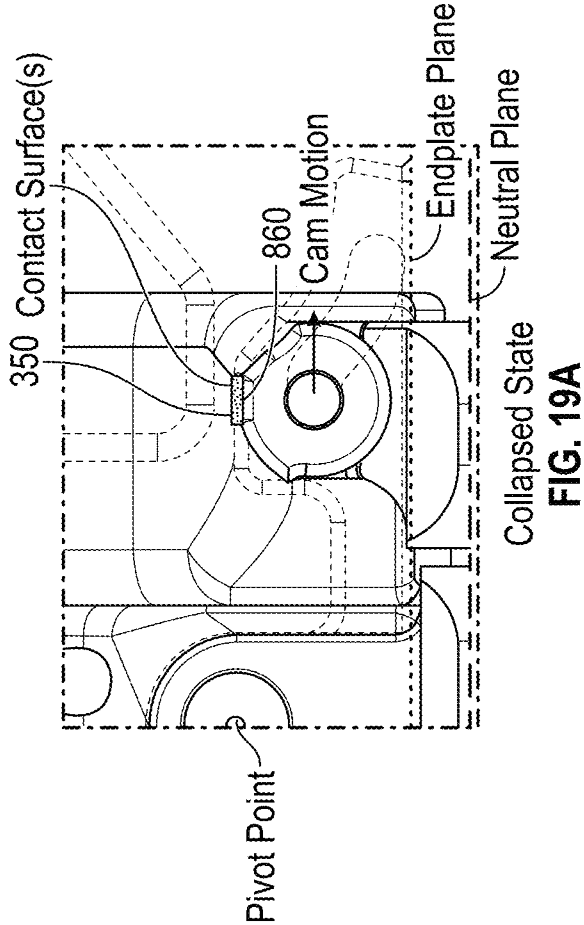
FIGS. 19A, 19B, 19C, and 19D are section side views of the expandable intervertebral implant of FIG. 1 showing the engagement of the angulation cam for various states of expansion according to an embodiment of the present disclosure.

FIGS. 19A, 19B, 19C, and 19D are section side views of the expandable intervertebral implant 2000 showing the engagement of an angulation cam 800 for various states of expansion according to an embodiment of the present disclosure. FIG. 19A shows the expandable intervertebral implant 2000 in a collapsed state wherein an endplate plane and a neutral plane are generally parallel. In the collapsed state the second cam surface 860 of the angulation cam 800 may be in contact with the first cam engagement surface 350 of the height saddle 300.

Figure 19B:
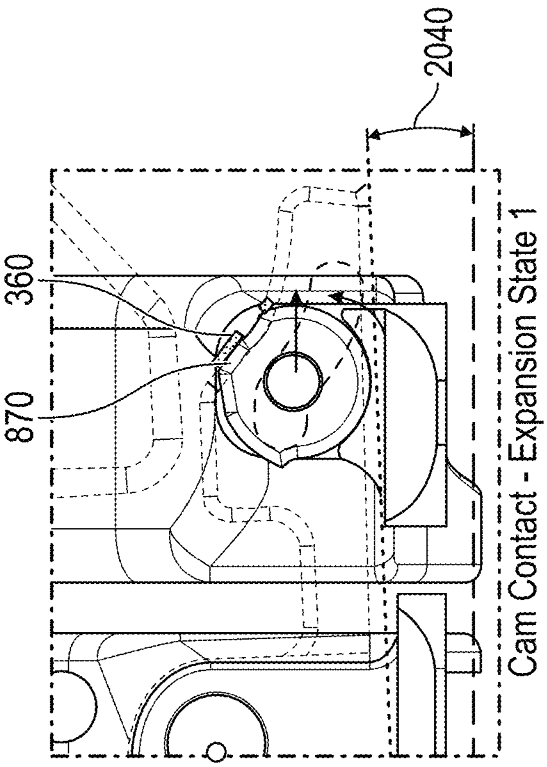

FIG. 19B shows the expandable intervertebral implant 2000 in a first expansion state, wherein an expansion angle 2040 between the endplate plane and the neutral plane may be greater than zero. One or more angulation cams 800 may translate and/or rotate along one or more cam slots 310 of the height saddle 300, in response to clock-wise rotation of the angulation screw 600, from the collapsed state to the first expansion state. In the first expansion state the third cam surface 870 of the angulation cam 800 may be in contact with the second cam engagement surface 360 of the height saddle 300.

Figure 19C:
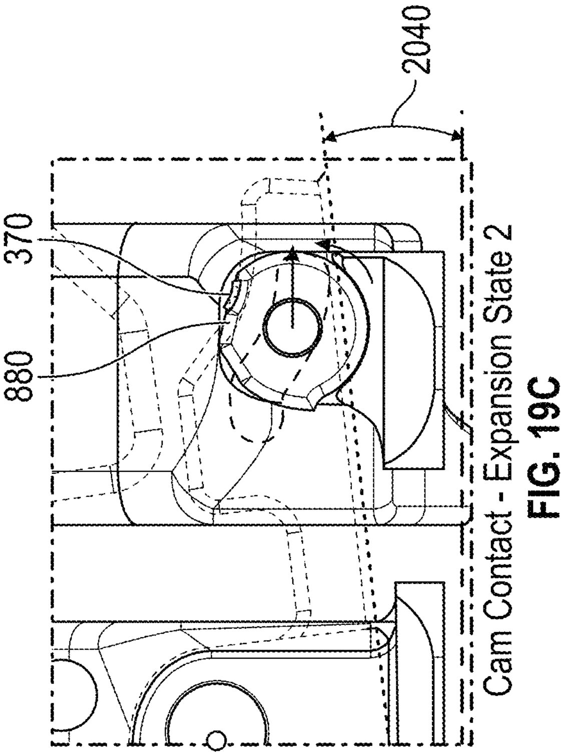

FIG. 19C shows the expandable intervertebral implant 2000 in a second expansion state, wherein the expansion angle 2040 between the endplate plane and the neutral plane may be greater than the expansion angle 2040 in the first expansion state. One or more angulation cams 800 may translate and/or rotate along one or more cam slots 310 of the height saddle 300, in response to clock-wise rotation of the angulation screw 600, from the first expansion state to the second expansion state. In the second expansion state the fourth cam surface 880 of the angulation cam 800 may be in contact with the third cam engagement surface 370 of the height saddle 300.

Figure 19D:
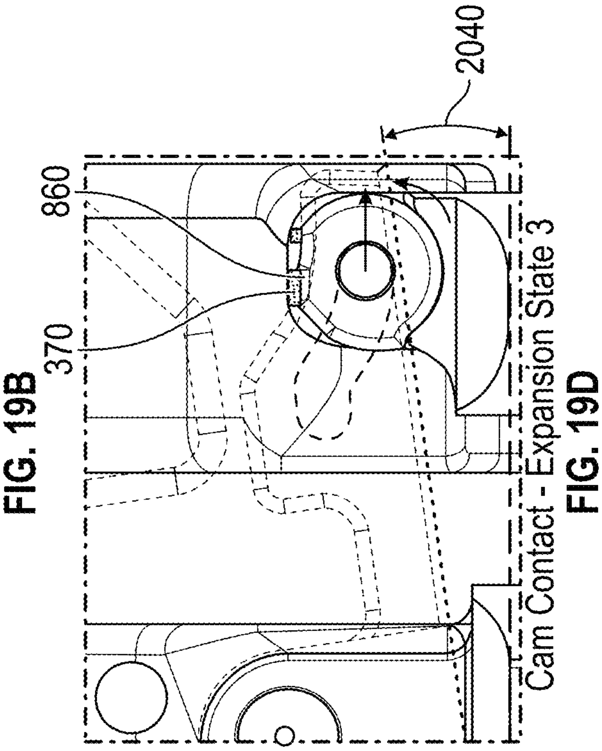

FIG. 19D shows the expandable intervertebral implant 2000 in a third expansion state, wherein the expansion angle 2040 between the endplate plane and the neutral plane may be greater than the expansion angle 2040 in the second expansion state. One or more angulation cams 800 may translate and/or rotate along one or more cam slots 310 of the height saddle 300, in response to clock-wise rotation of the angulation screw 600, from the second expansion state to the third expansion state. In the third expansion state the second cam surface 860 of the angulation cam 800 may be in contact with the third cam engagement surface 370 of the height saddle 300.

An actuation device, external to an expandable intervertebral implant 2000, may include one or more pairs of angled surfaces and/or one or more cam mechanisms configured to engage the expandable intervertebral implant 2000. The actuation device may be configured to removably engage the expandable intervertebral implant 2000. The actuation device may be configured to actuate height expansion and/or angular expansion of the expandable intervertebral implant 2000. Additionally, the expandable intervertebral implant 2000 may be configured to retain the height expansion and/or angular expansion driven by the actuation device.

The expandable intervertebral implant 2000 may be manufactured from titanium alloy, titanium, stainless steel, cobalt chrome, PEEK, or other implant quality material with suitable mechanical properties. Additionally, or alternatively, one or more components of the expandable intervertebral implant 2000 may manufactured through additive manufacturing methods. In some embodiments, one or more components of the expandable intervertebral implant 2000 may include a porous surface. The porous surface may be configured to promote bone in-growth. The porous surface may be configured as a trabecular structure configured to promote bone in-growth. Additionally, or alternatively, the porous surface may be configured to include cells that are configured to receive biologic material prior to implantation to promote bone in-growth after implantation. Additionally, or alternatively, the porous surface may be configured to include less metal mass implanted and more open areas for the bone to grow through the implant and create a more rigid fusion of the superior vertebra and inferior vertebra. In an embodiment, one or more components of the expandable intervertebral implant 2000 may be additively manufactured with integrated porous features configured for bone integration.

The expandable intervertebral implant 2000 may have flexible or compliant structures to perform or maintain expansion. The expandable intervertebral implant 2000 may have a single superior/inferior endplate component having a living hinge in place of a superior endplate 100 configured to be rotatably connected to an inferior endplate 200 and one or more endplate pins 1200.

Reference throughout this specification to "an embodiment" or "the embodiment" means that a particular feature, structure or characteristic described in connection with that embodiment is included in at least one embodiment. Thus, the quoted phrases, or variations thereof, as recited throughout this specification are not necessarily all referring to the same embodiment.

Similarly, it should be appreciated that in the above description of embodiments, various features are sometimes grouped together in a single embodiment, Figure, or description thereof for the purpose of streamlining the disclosure. This method of disclosure, however, is not to be interpreted as reflecting an intention that any claim require more features than those expressly recited in that claim. Rather, as the following claims reflect, inventive aspects lie in a combination of fewer than all features of any single foregoing disclosed embodiment. Thus, the claims following this Detailed Description are hereby expressly incorporated into this Detailed Description, with each claim standing on its own as a separate embodiment. This disclosure includes all permutations of the independent claims with their dependent claims.

The phrases "generally parallel" and "generally perpendicular" refer to structures that are within 30° parallelism or perpendicularity relative to each other, respectively. Recitation in the claims of the term "first" with respect to a feature or element does not necessarily imply the existence of a second or additional such feature or element. Elements recited in means-plus-function format are intended to be construed in accordance with 35 U.S.C. § 112 Para. 6. It will be apparent to those having skill in the art that changes may be made to the details of the above-described embodiments without departing from the underlying principles of the disclosure.

While specific embodiments and applications of the present disclosure have been illustrated and described, it is to be understood that the disclosure is not limited to the precise configuration and components disclosed herein. Various modifications, changes, and variations which will be apparent to those skilled in the art may be made in the arrangement, operation, and details of the methods and systems of the present disclosure without departing from its spirit and scope.

The invention claimed is:

1. An expandable intervertebral implant comprising:
- a superior end plate configured to engage a superior vertebra;
- an inferior end plate configured to engage an inferior vertebra, wherein the inferior endplate is spaced apart from the superior end plate by a gap;
- a first slider moveable along a first direction;
- a first screw configured to rotatably engage the first slider to urge only linear expansion of the gap;
- a second screw configured to rotatably engage a second slider to urge only angular expansion of the gap; and
- one or more cams each coupled to the second slider;
- wherein:
- the first screw and the second screw are independently engageable from the same direction by a first driver tool and a second driver tool respectively; and
- the one or more cams are configured to urge angular expansion of the gap in response to at least one of:
- rotation of the one or more cams about a rotation axis; and
- motion of the one or more cams along the first direction.

2. The expandable intervertebral implant of claim 1, wherein:
- the second slider is threadably coupled to the first slider;
- the second slider is moveable along the first direction;
- the second slider is moveable independent of the first slider; and
- movement of the second slider results in at least one of:
- rotation of the one or more cams about the rotation axis; and
- motion of the one or more cams along the first direction.

3. The expandable intervertebral implant of claim 2, wherein:
- the first screw extends along an anterior-posterior direction;
- the first direction comprises the anterior-posterior direction; and
- rotation of the first screw results in movement of the first slider in the anterior-posterior direction.

4. The expandable intervertebral implant of claim 3, wherein the second screw is captive relative to the first slider.

5. The expandable intervertebral implant of claim 3,
- wherein the second screw is configured to rotate to urge movement of the second slider in the anterior-posterior direction.

6. The expandable intervertebral implant of claim 5, wherein the first screw is captive relative to the superior endplate.

7. The expandable intervertebral implant of claim 1, wherein the one or more cams are configured to be rotatable and translatable relative to the superior endplate and the inferior endplate.

8. The expandable intervertebral implant of claim 1, wherein the second slider is moveable in a second direction, opposite the first direction, to urge only angular expansion of the gap.

9. An expandable intervertebral implant comprising:
- a superior end plate configured to engage a superior vertebra;
- an inferior end plate configured to engage an inferior vertebra, wherein the inferior endplate is spaced apart from the superior end plate by a gap;
- one or more cams configured to be translatable relative to the superior endplate and the inferior endplate;
- a first screw extending along an anterior-posterior direction; and
- a first slider configured to threadably receive the first screw;
- wherein:
- the first screw is actuatable from an anterior end of the implant;
- the first screw is configured to rotate to urge translation of the first slider in the anterior-posterior direction;

the one or more cams are coupled to the first slider such that translation of the first slider in the anterior-posterior direction results in translation of the one or more cams;

the one or more cams are configured to urge angular expansion of the gap in response to translation of the one or more cams; and the angular expansion results in the anterior end of the implant expanding more than a posterior end of the implant.

10. The expandable intervertebral implant of claim 9, further comprising a second slider threadably coupled to the first slider and a second screw extending along the anterior-posterior direction, wherein:

the second slider is moveable along the anterior-posterior direction;

the second screw is configured to rotate to urge movement of the second slider in the anterior-posterior direction; and movement of the second slider urges linear expansion of the gap.

11. The expandable intervertebral implant of claim 10, wherein the first slider is moveable independent of the second slider.

12. The expandable intervertebral implant of claim 10, wherein movement of the second slider results in comparable movement of the first slider and movement of the first slider does not result in movement of the second slider.

13. The expandable intervertebral implant of claim 9, wherein the one or more cams are further configured to be rotatable relative to the superior endplate and the inferior endplate, wherein translation of the first slider in the anterior-posterior direction results in rotation of the one or more cams, and the one or more cams are configured to urge angular expansion of the gap in response to rotation of the one or more cams.

14. The expandable intervertebral implant of claim 9, further comprising:

an anterior height comprising a first distance, in a superior-inferior plane, between a superior anterior portion and an inferior anterior portion; and a posterior height comprising a second distance, in the superior-inferior plane, between a superior posterior portion and an inferior posterior portion;

wherein, in response to rotation of the one or more cams about a medial-lateral axis, the one or more cams are configured to urge angular expansion of the gap by increasing the anterior height more than the posterior height.

15. The expandable intervertebral implant of claim 9, wherein the one or more cams are received within one or more cam slots, and the one or more cam slots are configured to urge rotation of the one or more cams relative to the first slider in response to translation of the one or more cams within the one or more cam slots.

16. An expandable intervertebral implant comprising:

a superior end plate configured to engage a superior vertebra;

an inferior endplate configured to engage an inferior vertebra, wherein the inferior endplate is spaced apart from the superior endplate by a gap such that the expandable intervertebral implant comprises:

an anterior height comprising a first distance, in a superior-inferior plane, between a superior anterior portion of the superior endplate and an inferior anterior portion of the inferior end plate; and a posterior height comprising a second distance, in the superior-inferior plane, between a superior posterior portion and an inferior posterior portion; and a first cam configured to rotate about a medial-lateral axis such that the gap expands linearly and angularly by:

increasing the posterior height; and increasing the anterior height more than the posterior height;

wherein the first cam is configured to translate anteriorly and superiorly following a non-linear cam engagement surface to increase the anterior height.

17. The expandable intervertebral implant of claim 16, further comprising a first slider coupled to the first cam, wherein:

the first slider is moveable along an anterior-posterior direction; and movement of the first slider results in at least one of:

rotation of the first cam about the medial-lateral axis; and motion of the first cam along the anterior-posterior direction.

18. The expandable intervertebral implant of claim 17, further comprising a first screw, extending along the anterior-posterior direction, configured to rotatably engage the first slider, wherein the first screw is configured to rotate to urge movement of the first slider in the anterior-posterior direction.

19. The expandable intervertebral implant of claim 17, further comprising a second slider moveable along the anterior-posterior direction to urge linear expansion of the gap.

20. The expandable intervertebral implant of claim 16, wherein, in response to translation of the first cam, the first cam is configured to urge angular expansion of the gap by increasing the anterior height more than the posterior height.

21. The expandable intervertebral implant of claim 20, wherein the first cam is received within a cam slot, and the cam slot comprises the non-linear cam engagement surface.

22. The expandable intervertebral implant of claim 16, further comprising a first screw and a second screw, wherein:

rotation of the first screw urges expansion of the gap angularly by increasing the anterior height more than the posterior height; and rotation of the second screw urges expansion of the gap linearly by increasing the anterior height and the posterior height equally.

23. The expandable intervertebral implant of claim 22, further comprising an anterior opening configured to receive a driver configured to engage the first screw.

* * * * *